US008333750B2

(12) United States Patent
Tanaka et al.

(10) Patent No.: US 8,333,750 B2
(45) Date of Patent: Dec. 18, 2012

(54) LABEL, MEDICINE BAG AND STORAGE CONTAINER WITH THE LABEL

(75) Inventors: Shinya Tanaka, Matsusaka (JP); Kiyoko Enosaki, Osaka (JP); Katsunori Takasugi, Odate (JP); Yoshiharu Yamaguchi, Ichinomiya (JP)

(73) Assignee: Nipro Corporation, Osaka (JP)

( * ) Notice: Subject to any disclaimer, the term of this patent is extended or adjusted under 35 U.S.C. 154(b) by 983 days.

(21) Appl. No.: 11/919,256

(22) PCT Filed: Apr. 28, 2006

(86) PCT No.: PCT/JP2006/308995

§ 371 (c)(1),
(2), (4) Date: May 15, 2008

(87) PCT Pub. No.: WO2006/118252

PCT Pub. Date: Nov. 9, 2006

(65) Prior Publication Data

US 2008/0275421 A1 Nov. 6, 2008

(30) Foreign Application Priority Data

Apr. 28, 2005 (JP) ................................ 2005-132915

(51) Int. Cl.
*A61B 19/00* (2006.01)

(52) U.S. Cl. ....................................................... 604/404

(58) Field of Classification Search .......... 604/403–416; 283/81; 206/459.5; 428/43

See application file for complete search history.

(56) References Cited

U.S. PATENT DOCUMENTS 4,526,404 A 7/1985 Vazquez
5,217,307 A 6/1993 McClintock
5,782,495 A * 7/1998 Grosskopf et al. .............. 283/81
2004/0188281 A1 9/2004 Iwasa et al.

FOREIGN PATENT DOCUMENTS

| | | | |
|---|---|---|---|
| JP | 45-30358 | | 11/1970 |
| JP | 6-33172 | U | 4/1994 |
| JP | 6-39713 | Y2 | 10/1994 |
| JP | 3074885 | U | 11/2000 |
| JP | 2002-132161 | A | 5/2002 |
| JP | 2004-173810 | A | 6/2004 |
| JP | 3105885 | U | 9/2004 |
| JP | 2004-305722 | A | 11/2004 |
| JP | 2005-107110 | A | 4/2005 |
| JP | 2005-245983 | A | 9/2005 |
| WO | WO-92/19284 | A1 | 11/1992 |

* cited by examiner

*Primary Examiner* — Philip R Wiest

(74) *Attorney, Agent, or Firm* — Birch, Stewart, Kolasch & Birch, LLP

(57) ABSTRACT

A label enables a user to recognize information necessary when using a medicine bag in a reliable fashion. The label includes a base part indicating thereon basic information including at least information on ingredients of medicines accommodated in a medicine bag and a detachable part detachably joined to the base part. The detachable part is so shaped as to be attachable to such an area of the medicine bag that it becomes difficult to use the medicine bag when a surface of the area is covered, and the detachable part indicates thereon characteristic information including at least directions on use of the medicine bag.

15 Claims, 15 Drawing Sheets

LABEL, MEDICINE BAG AND STORAGE CONTAINER WITH THE LABEL

TECHNICAL FIELD

The present invention relates to a label indicating specific information.

BACKGROUND ART

Medicine bags which are hung from a stand pole or the like when in use are commonly known (e.g., patent document 1).

A medicine bag of this kind is a pouchlike medicine container provided with a hanging hole formed at one end and a medicinal fluid discharge port formed at the other end, the medicine bag being made to allow a medicinal fluid to be discharged through the port under conditions where the medicine bag is hung from a stand pole or the like by use of the hole.

A medicine bag of patent document 1 is configured such that the interior of the medicine bag is divided into two chambers by a breakable partition wall to accommodate different kinds of medicines in these chambers and, before the medicine bag is used, these chambers are connected to each other, making it possible to mix the individual medicines inside the medicine bag.

The above kind of medicine bag is provided with a label attached thereto in many cases, the label indicating information (hereinafter referred to as basic information) on the medicine bag itself, such as ingredients of medicines accommodated therein. This label also indicates information (hereinafter referred to as characteristic information) concerning directions on use of the medicine bag, such as how to interconnect the chambers, together with the medicine ingredients or the like.

Since the label indicates the basic information and the characteristic information in a uniform manner, however, it has been impossible to enable a user to recognize when using the medicine bag the characteristic information which, particularly needs to be conveyed to the user at the time of use of the medicine bag.

The present invention has been made in light of the problem. Accordingly, it is an object of the invention to provide a label which enables a user to recognize information necessary when using a medicine bag in a reliable fashion.

[Patent document 1] Japanese Examined Utility Model Application Publication No. HEI6-39713

DISCLOSURE OF THE INVENTION

To solve the problem, the present invention provides a label to be attached to a medicine bag accommodating medicines, the label including a base part indicating thereon basic information including at least information on ingredients of the medicines accommodated in the medicine bag, and a detachable part detachably joined to the base part, the label being characterized in that the detachable part is so shaped as to be attachable to such an area of the medicine bag that it becomes difficult to use the medicine bag when a surface of the area is covered, and the detachable part indicates thereon characteristic information including at least directions on use of the medicine bag.

According to the label of this invention, the characteristic information is indicated on the separately formed detachable part. This layout on the label not only allows for differentiation between the characteristic information and the basic information indicated on the base part but enables a user to recognize the characteristic information in a reliable fashion because the detachable part can be attached to such an area of the medicine bag that the detachable part attached thereto would hinder the use of the medicine bag.

Specifically, when using the medicine bag, the user would tear off the detachable part attached to the area from the base part. It is possible to enable the user to visually recognize the characteristic information at this time, since the characteristic information is indicated on the detachable part.

Therefore, according to the label of the present invention, it is possible to enable the user to securely recognize the characteristic information which is necessary when using the medicine bag.

Also, the present invention provides a medicine bag including the label, a container body accommodating medicines in an internal space thereof, the container body having a hanging hole formed in one end, and a port formed at the other end of the container body, the medicine bag being characterized in that the detachable part of the label is so attached as to cover at least part of the hanging hole, and the medicines in the container body are discharged through the port under conditions where the container body is suspended by the hanging hole.

According to the medicine bag of this invention, the detachable part closes off the hanging hole and, thus, it is possible to enable the user to recognize the characteristic information indicated on the detachable part in a reliable fashion when the user is going to peel off the detachable part to open the hanging hole at the time of use of the medicine bag. This arrangement serves to prevent the user's failure to follow a correct operating procedure, for instance.

Further, the present invention provides a medicine bag including the label, a container body accommodating medicines in an internal space thereof, the container body having a hanging hole formed in one end, and a port formed at the other end of the container body, the medicine bag being characterized in that the detachable part of the label is so attached as to cover at least part of the port, and the medicines in the container body are discharged through the port under conditions where the container body is suspended by the hanging hole.

According to the medicine bag of this invention, the detachable part closes off the port and, thus, it is possible to enable the user to recognize the characteristic information indicated on the detachable part in a reliable fashion when the user is going to peel off the detachable part to open the port at the time of use of the medicine bag. This arrangement serves to prevent the user's failure to follow a correct operating procedure, for instance.

Also, the present invention provides a label to be attached to a specific object, the label including a base part, and a detachable part detachably joined to the base part along a tear-off line having a defined tearing direction, the label being characterized in that there is formed a recessed part having a rounded bottom portion in an edge portion of the base part and the detachable part, the bottom portion extending along both of the base part and the detachable part, and the tear-off line includes a tearing slit which makes the edge portion of the base part and the detachable part tearable from each other at an upstream end of the tearing direction and a perforation located downstream of the tearing slit along the tearing direction, wherein the tearing slit is so arranged as to be oriented in a direction intersecting the bottom portion of the recessed part.

According to the label of this invention, the tearing slit is formed along the direction intersecting the bottom portion of the recessed part (toward the direction intersecting the bottom portion of the recessed part). It is therefore possible to transmit a force applied to the detachable part from an upstream side of aforementioned tearing direction along the edge portion of the detachable part forming the recessed part and redirect the force from the bottom portion of the recessed part into the intersecting direction, so that the force is transmitted to the tearing slit. Thus, according to this construction, the force applied to the detachable part can be efficiently transmitted to the tearing slit as a force acting along the tearing direction, so that the base part and the detachable part can easily be torn apart.

One possible approach to efficiently transmitting the force applied to the detachable part might be to form the tearing slit on an extended line of the edge of the tearing slit constituting a side portion of the recessed part (or the portion located more outward than the bottom portion). This approach however has had a problem that the force applied to the detachable part would not be transmitted to the tearing slit but toward the bottom portion in a boundary area between the side portion and the bottom portion, thereby producing a problem that the base part and the detachable part would be torn apart from the bottom portion.

Conversely, another possible approach might be to form the tearing slit on an extended line of the edge portion of the base part constituting a side portion of the recessed part. In this case, however, there is a likelihood that the force applied to the detachable part acts as a force which tears apart the label at the bottom portion before the force reaches a boundary area between the side portion and the bottom portion.

According to the label of the present invention, the tearing slit is so formed as to intersect the bottom portion of the recessed part, so that the force applied to the detachable part can be efficiently transmitted to the tearing slit as a force acting along the tearing direction and, as a consequence, the base part and the detachable part can easily be torn apart.

Here, the expression concerning the tearing slit that "makes the edge portion of the base part and the detachable part tearable apart" refers not only to an arrangement in which the edge portion of the base part and the detachable part is already torn apart over a specified range but also to an arrangement in which a slit passing through the base part and the detachable part in a thickness direction thereof is formed at a downstream position of the tearing direction at an extremely small distance from the edge portion of the base part and the detachable part. In other words, the expression includes an arrangement in which the slit is formed to allow the base part and the detachable part to be torn apart by as much as the extremely small distance when a specific force is applied to the tab portion.

Also, the expression "the direction intersecting the bottom portion of the recessed part" refers to a direction other than a tangential direction of the bottom portion having a rounded shape, wherein the direction along the tearing slit intersects the bottom portion at a specific angle.

Furthermore, the present invention provides a storage container including a container body, a cap for sealing the container body which can be unsealed by operating the cap in a specified opening direction thereof, and the label, the storage container being characterized in that the base part of the label is attached to the container body and the detachable part of the label is attached to the cap under conditions where the tearing direction of the tear-off line of the label aligns with the opening direction of the cap.

According to this invention, the label is attached to the container body and the cap under conditions where the opening direction of the cap aligns with the tearing direction of the tear-off line, so that the detachable part and the base part can be torn apart by operating the cap in the opening direction thereof.

BRIEF DESCRIPTION OF THE DRAWINGS

FIG. 4 is a diagram showing areas where an adhesive layer is formed on a detachable part of the label of FIG. 2, in which

FIG. 7 shows a medicine bag according to another embodiment of the present invention, in which

FIG. 14 shows a label according to still another embodiment of the present invention, in which

BEST MODES FOR CARRYING OUT THE INVENTION

Preferred embodiments of the present invention are now described with reference to the drawings below.

Figure 1A:
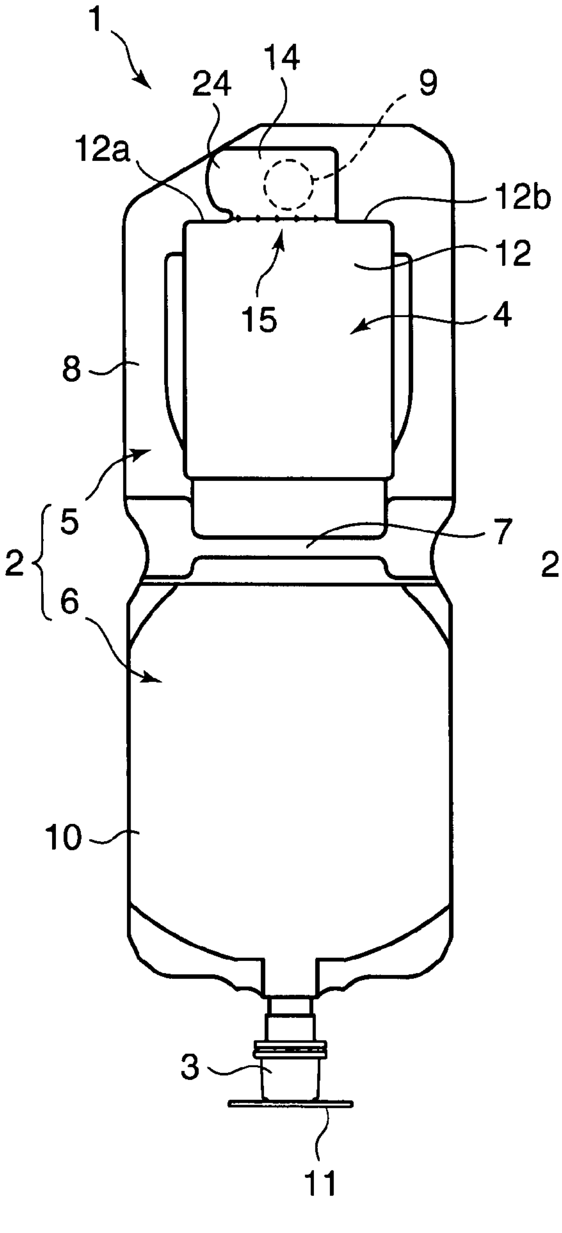
FIG. 1A is a plan view showing the overall construction of a medicine bag according to the present invention and FIG. 1B is a plan view schematically showing the internal construction of the medicine bag of FIG. 1A.
Figure 1B:
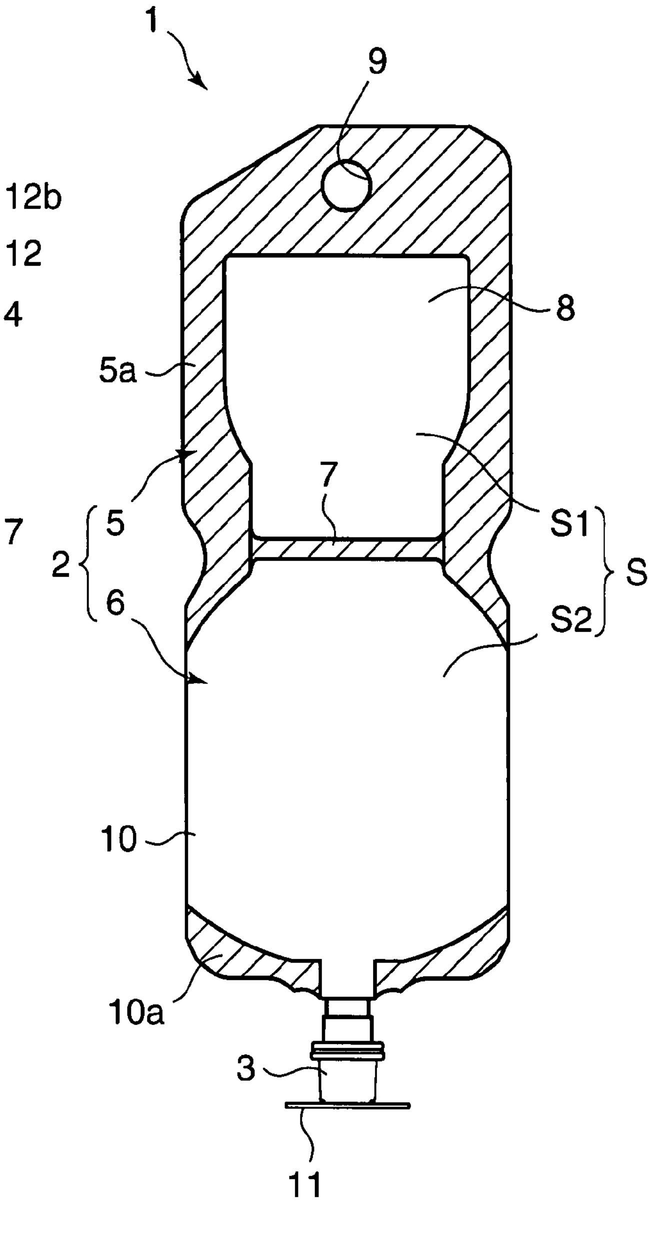

FIG. 1A is a plan view showing the overall construction of a medicine bag according to the present invention and FIG. 1B is a plan view schematically showing the internal construction of the medicine bag of FIG. 1A.

Referring to FIG. 1, the medicine bag 1 includes a container body 2 for accommodating medicines, a port 3 through which the medicines in the container body 2 can be discharged and a label 4 attached to a front surface of the container body 2.

The container body 2 has as a basic construction a powder container 5 for accommodating a powder medicine and a liquid container 6 for accommodating a liquid medicine, the powder container 5 and the liquid container 6 being joined in series via a weak seal part 7. The container body 2 is configured such that the powder medicine and the liquid medicine can be mixed in the container body 2 by opening the weak seal part 7. In the following discussion, the container body 2 is described on the assumption that a side on which the powder container 5 is disposed is the top side.

The powder container 5 is configured to form a downwardly opening container by joining a pair of facing sheets 8 (Figure shows one sheet only) in a U-shape by joining the sheets 8 along a strong seal part 5*a*. In a top part of this powder container, there is formed a hanging hole 9 passing through the two sheets in a thickness direction thereof.

The liquid container 6 is configured to form a container by joining top and bottom parts of facing sheet portions of a tubular sheet 10.

The port 3 is inserted into a bottom opening of the tubular sheet 10 between the facing sheet portions thereof and, in this condition, inner surfaces of the facing sheet portions, or the facing sheet portions and an outer surface of the port 3, are joined to one another along a strong seal part 10*a*.

There is formed a medicine storage space S in the container body 2 and this medicine storage space S is partitioned into a powder storage chamber S1 and a liquid storage chamber S2 by the weak seal part 7 formed between the powder container 5 and the liquid container 6 in the manner.

Specifically, the weak seal part 7 is formed by joining the facing sheets 8 or the facing sheet portions of the tubular sheet 10 with a weaker joint strength than the strong seal part 5*a* or 10*a*. Therefore, it is possible to interconnect the powder storage chamber S1 and the liquid storage chamber S2 by breaking apart the weak seal part 7 by compressing the liquid container 6 from outside to increase an internal pressure thereof when using the medicine bag 1.

The port 3 is a tubular member for interconnecting the medicine storage space S and the exterior. This port 3 incorporates an unillustrated elastic element disposed in a downwardly exposed state. It is possible to discharge the medicine in the medicine storage space S by piercing this elastic element with an unillustrated needle. A bottom surface of the port 3 is covered by a tamper seal 11 which proves that the port 3 has not been opened yet.

Figure 2:
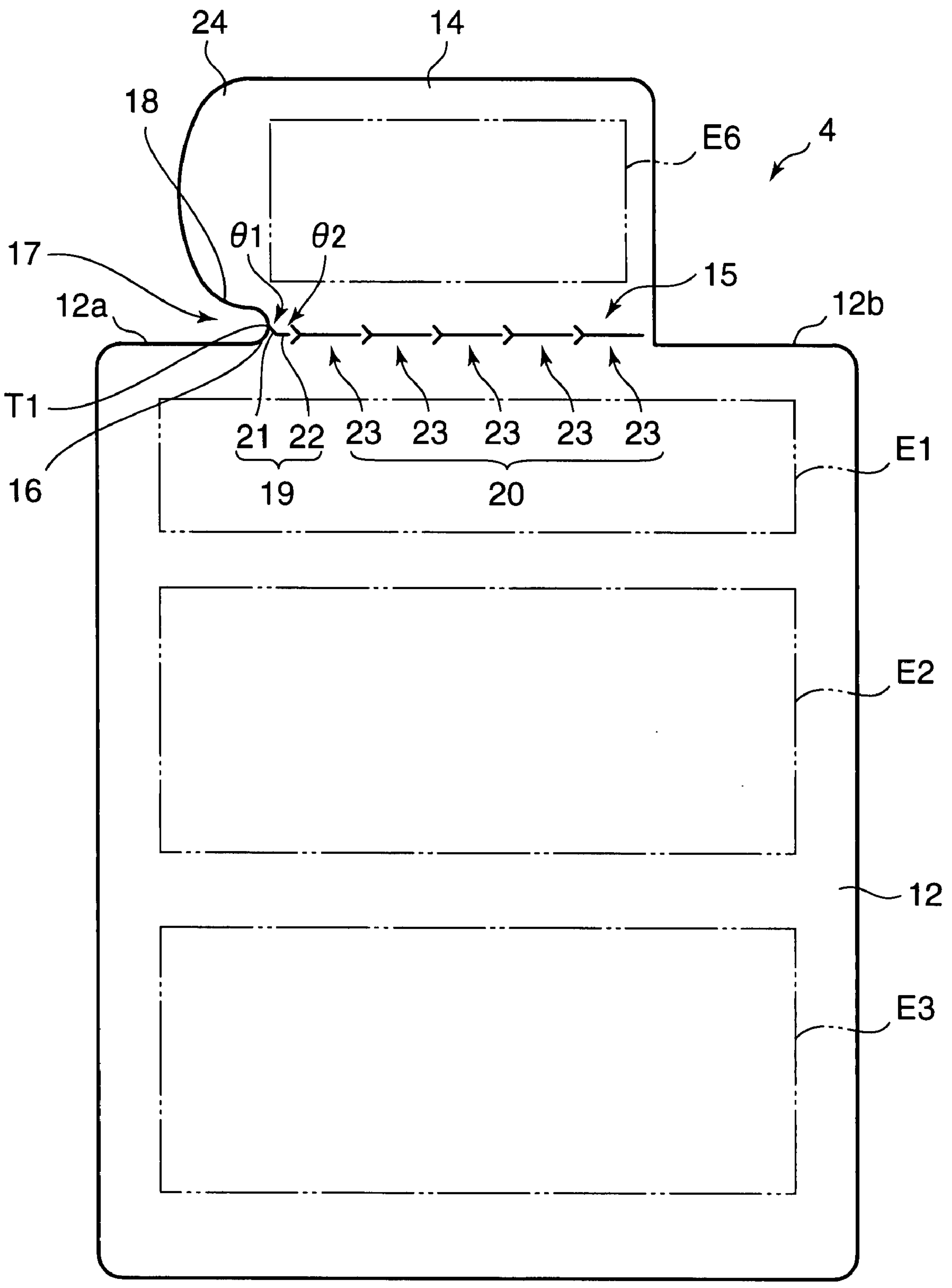
FIG. 2 is a plan view showing a label attached to the medicine bag of FIG. 1.
Figure 3:
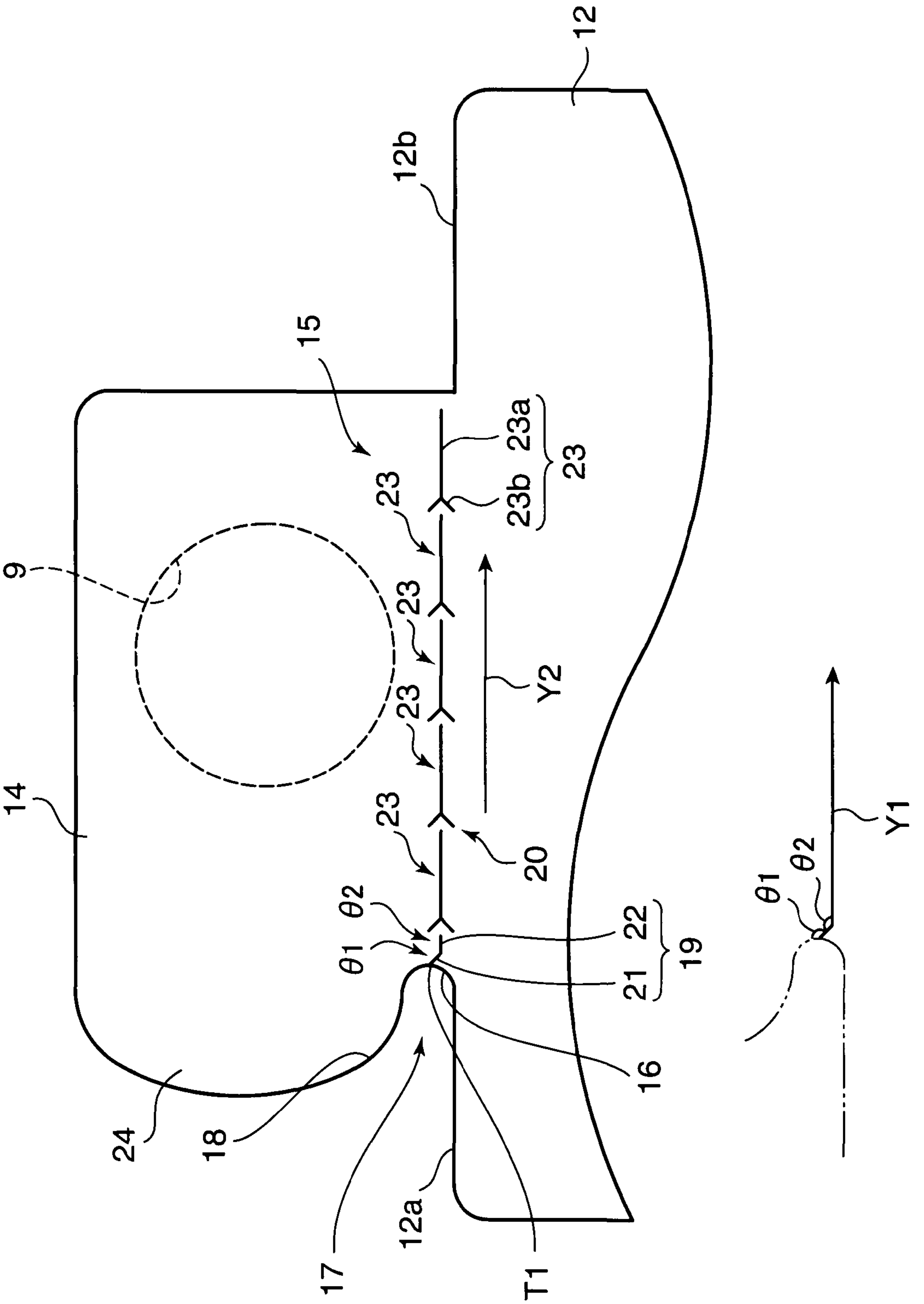
FIG. 3 is a fragmentary schematic plan view showing an enlarged view of a principal part of the label of FIG. 2.

FIG. 2 is a plan view showing the label 4 attached to the medicine bag of FIG. 1. FIG. 3 is a fragmentary schematic plan view showing an enlarged view of a principal part of the label 4 of FIG. 2.

Referring to FIGS. 1 through 3, the label 4 includes a generally rectangular base part 12 and a detachable part 14 extending upward from the base part 12 by way of a left shoulder portion 12*a* and a right shoulder portion 12*b*. Between the base part 12 and the detachable part 14, there is formed a tear-off line 15 with a defined tearing direction Y1 (left to right as shown in the Figure).

Also, between the base part 12 and the detachable part 14, there is formed a leftward opening recessed part 17 having a generally semicircular (rounded) bottom portion 16 which extends along the two parts 12, 14. Specifically, the recessed part 17 is formed into a U-shape which connects from a curved portion 18 of the detachable part 14 curving along a left edge thereof toward the tear-off line 15 to the bottom portion 16, the bottom portion 16 connecting to the shoulder portion 12*a* of the base part 12.

The tear-off line 15 includes a tearing slit 19 where a left edge portion of the base part 12 and the detachable part 14 is cut apart at an upstream end of the tearing direction Y1 and a perforation 20 laid out below the tearing slit 19 (closer to the base part 12).

The tearing slit 19 includes an introductory portion 21 extending from a bottommost point T1 of the bottom portion 16 and a bent portion 22 bending away from the introductory portion 21. The introductory portion 21 intersects the bottom portion 16 in such a way that an angle θ1 formed therebetween, opening toward the detachable part 14, becomes an obtuse angle. The bent portion 22 bends away from the introductory portion 21 in such a way that an angle θ2 formed therebetween, opening toward the detachable part 14, becomes an obtuse angle, the bent portion 22 being arranged on a line extended in a tearing direction Y2 along the perforation 20.

In the label 4, a tearing start point (i.e., the bottommost point T1 of the bottom portion 16) and the perforation 20 are vertically offset and there is provided the tearing slit 19 interconnecting both along a gentle slope as described above. For this reason, a force applied to the detachable part 14 is transmitted from an arc-shaped segment of the bottom portion 16 through the tearing slit 19, and from the tearing slit 19 through the perforation 20, in two steps along gently changing directions. Therefore, according to the label 4, it is possible to prevent breakage of other portions thereof than the tear-off line 15 when the base part 12 and the detachable part 14 are detached from each other.

The perforation 20 is made of a plurality of slits 23 arranged along the tearing direction Y2, the slits 23 passing through the label 4 in a thickness direction thereof. Each of the slits 23 is formed into a Y-shape having a leg portion 23*a* arranged along the tearing direction Y2 and a V-shaped portion 23*b* opening leftward, so that the label 4 can be torn off along the leg portions 23*a* with the V-shaped portions 23*b* keeping a broken part of the label 4 from deviating from the tearing direction Y2 when the label 4 is torn off along the tear-off line 15 from left.

The base part 12 is attached to a front surface area of the powder storage chamber S1 by means of an adhesive layer formed over an almost entire rear surface area of the base part 12. On a front surface of the base part 12, there are provided a product name indicating area E1, an ingredients indicating area E2 and a lot number indicating area E3 in this order from a side of the detachable part 14.

The product name indicating area E1 indicates product name of the medicine bag, type of product, and so on.

The ingredients indicating area E2 indicates basic information including ingredients and quantities of the medicines accommodated in the medicine storage space S, a manufacturer/distributor or a distributor, or precautions on use, for instance.

The lot number indicating area E3 indicates a lot number of the medicine bag 1, expiration data or the name of a patient for whom the medicine bag 1 is used, for instance.

On the other hand, the detachable part 14 is attached to the front surface of the powder container 5, covering the hanging hole 9. While an adhesive layer may be formed over an almost entire rear surface area of the detachable part 14, it is preferable to form areas uncovered by the adhesive layer as shown by hatching in FIG. 4.

Figure 4A:
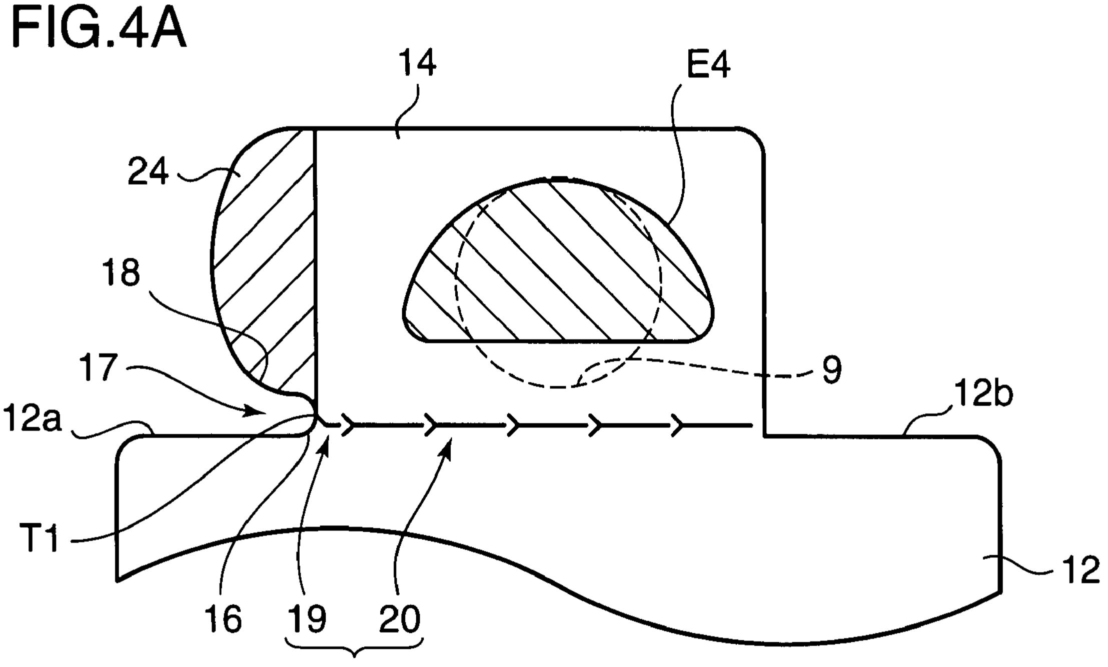
FIG. 4A shows an arrangement in which two areas uncovered by the adhesive layer are formed and FIG. 4B shows an arrangement in which one area uncovered by the adhesive layer is formed.
Figure 4B:
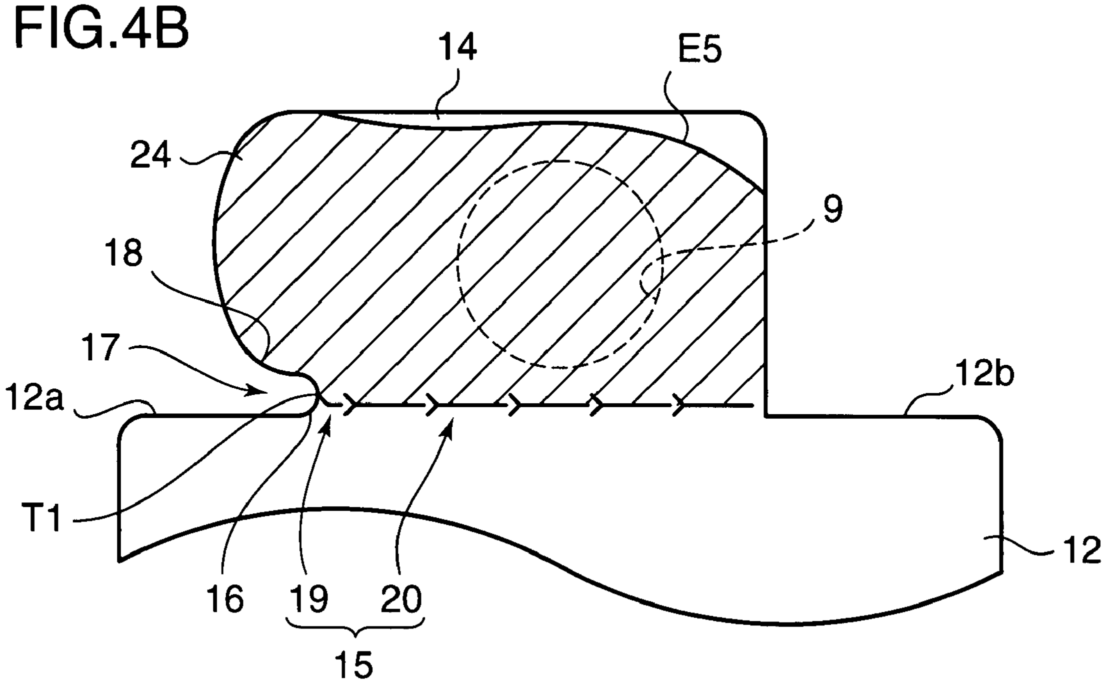

Specifically, as illustrated in FIG. 4A, a rear surface area of the detachable part 14 between the left edge thereof and a boundary line extending upward from the bottommost point T1 of the bottom portion 16 is not covered by the adhesive layer and this area forms a tab portion 24. The rear surface of the detachable part 14 is not covered by the adhesive layer in an area E4 corresponding to the hanging hole 9 either, and this arrangement serves to prevent, foreign matter from adhering to the rear surface of the detachable part 14 through the hanging hole 9. Although an area corresponding to the tab portion 24 and the area E4 are not covered by the adhesive layer in an example shown in FIG. 4A, this arrangement may be modified such that the rear surface of the detachable part 14 is not covered by the adhesive layer in an area E5 including those areas as FIG. 4B.

Also, on a front surface of the detachable part 14, there is provided a characteristic information indicating area E6 for indicating characteristic information including at least directions on use of the medicine bag 1.

Written in the characteristic information indicating area E6 is information of which a user should be notified concerning the directions on use of the medicine bag 1, the information (characteristic information) including such an instruction that the user must open up the weak seal part 7 without fail before using the medicine bag 1.

Therefore, when hanging the medicine bag 1 from a stand pole or the like (not shown), the user will notice that the hanging hole 9 is covered by the detachable part 14 and attempt to peel off (tear off) the same. At this point, the user will visually inspect the characteristic information indicating area E6 and recognize that the weak seal part 7 must be broken apart.

To summarize, according to the medicine bag 1 of the foregoing embodiment, the detachable part 14 closes off the hanging hole 9 and, thus, it is possible to enable the user to recognize the characteristic information indicated on the detachable part 14 in a reliable fashion when the user is going to peel off the detachable part 14 to open the hanging hole 9 at the time of use of the medicine bag 1. This arrangement serves to prevent the user's failure to follow a correct operating procedure, for instance.

Also, according to the label 4 of the present embodiment, the characteristic information is indicated on the separately formed detachable part 14. This layout on the label 4 not only allows for differentiation between the characteristic information and the information indicated on the base part 12 but enables the user to recognize the characteristic information in a reliable fashion because the detachable part 14 can be attached to cover the hanging hole 9 in the medicine bag 1.

Specifically, when using the medicine bag 1, the user would tear off the detachable part 14 attached to cover the hanging hole 9 from the base part 12. It is possible to enable the user to visually recognize the characteristic information at this time, since the characteristic information is indicated on the detachable part 14.

Therefore, according to the label 4 of the foregoing embodiment, it is possible to enable the user to securely recognize the characteristic information which is necessary when using the medicine bag 1.

According to a construction in which the label 4 is provided with the tab portion 24 as in the foregoing embodiment, the user can easily separate the detachable part 14 from the base part 12 by holding the tab portion 24.

According to a construction in which the tearing start point of the tearing slit 19 and the perforation 20 are vertically offset and the tearing slit 19 forms obtuse angles (refer to θ1 and θ2 shown in FIG. 3) with both the bottom portion 16 of the recessed part 17 and the tearing direction Y2 along the perforation 20 as in the foregoing embodiment, a force applied to the tab portion 24 can be smoothly transmitted all the way along an edge of the detachable part 14 forming the recessed part 17, the tearing slit 19 and the perforation 20 in this order. For this reason, it is possible to prevent such a problem that a portion other than the tear-off line 15 breaks in an initial stage of lifting the tab portion 24.

One possible approach to allowing the detachable part 14 to be neatly torn off from the base part 12 might be to form a recessed part having a pointed bottom (such as a V-shaped recessed part) in an edge portion of the base part 12 and the detachable part 14 and to arrange the tear-off line 15 to extend from this edge portion (bottom). Practically, however, it is difficult to form an acutely pointed part corresponding to the recessed part in a label-making cutting tool. Therefore, in a strict sense, the bottom portion 16 of the recessed part 17 is rounded in shape.

If the bottom portion 16 of the recessed part 17 is formed into a rounded shape and the tear-off line is formed at right angles to the rounded shape at the bottommost point T1 thereof, the force applied to the tab portion 24 will be redirected by approximately 90 degrees at the tear-off line after the force has been transmitted halfway along an arc-shaped segment of the rounded shape. Consequently, there arises a possibility that a portion other than the tear-off line 15 may break when the force applied to the tab portion 24 is redirected.

Since the tearing start point (i.e., the bottommost point T1 of the bottom portion 16) and the perforation 20 are vertically offset and there is provided the tearing slit 19 interconnecting both along the gentle slope in the foregoing embodiment, the force applied to the tab portion 24 is transmitted from the arc-shaped segment of the bottom portion 16 through the tearing slit 19, and from the tearing slit 19 through the perforation 20, in two steps along gently changing directions.

Therefore, according to the label 4 of the foregoing embodiment, it is possible to prevent breakage of other portions thereof than the tear-off line 15 when the base part 12 and the detachable part 14 are detached from each other.

While the foregoing embodiment illustrates an example in which the tearing slit 19 intersects the bottom portion 16 of the recessed part 17 at an obtuse angle, the tearing slit 19 should preferably intersect the bottom portion 16 at least in such an intersecting direction that the angle θ1 becomes an angle other than 180 degrees (e.g., an acute angle). This arrangement makes it possible to transmit the force applied to the tab portion 24 along the edge of the detachable part 14 forming the recessed part 17 and redirect the force from the bottom portion 16 of the detachable part 14 into the intersecting direction, so that the force applied to the tab portion 24 can be efficiently transmitted to the tearing slit 19 as a force acting in the tearing direction Y1 and the base part 12 and the detachable part 14 can easily be separated from each other.

On the other hand, the tearing slit 19 according to the foregoing embodiment includes the introductory portion 21 which intersects the bottom portion 16 at an obtuse angle (refer to the angle θ1) and the bent portion 22 which bends away from the introductory portion 21 at an obtuse angle (refer to the angle θ2) and is arranged on the line extended in the tearing direction Y2 along the perforation 20. Therefore, the tearing slit 19 can transmit the force applied to the tab portion 24 in a more reliable fashion.

While the foregoing embodiment has been described with reference to a configuration in which the base part 12 is provided with the single detachable part 14, this detachable part 24 may be splittably configured.

Figure 5:
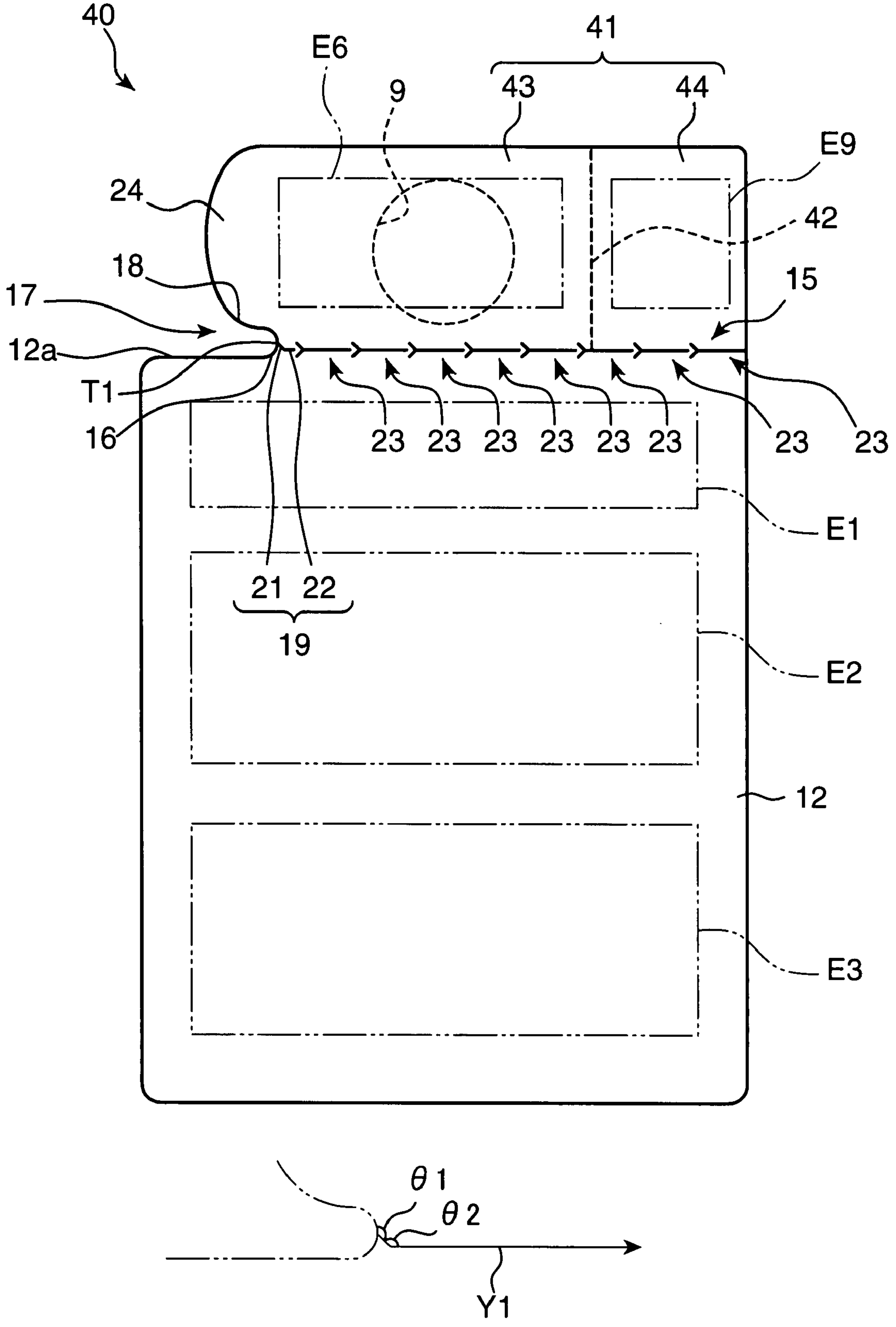
FIG. 5 is a developed plan view showing a label of which detachable part is splittably configured.

FIG. 5 is a plan view showing a label according to another embodiment of the present invention, in which elements configured like those of the foregoing embodiment are designated by the same symbols and a description of such elements is not given below.

Referring to FIG. 5, the label 40 according to the present embodiment includes the base part 12 and a detachable part 41 detachably joined thereto along the tear-off line 15.

The detachable part 41 includes a first detachable piece 43 and a second detachable piece 44 which are joined to each other splittably to left and right along a perforation (second tear-off line) 42 formed at right angles to the tearing direction Y1.

The first detachable piece 43 is made adhesively attachable to the medicine bag 1 in a manner that the first detachable piece 43 closes off the hanging hole 9 as in the foregoing embodiment. Also, there is provided the characteristic information indicating area E6 on the first detachable piece 43. The characteristic information indicating area E6 provides such indications as use of any medicine in the medicine bag 1 for injection purposes must be prohibited, or the user must make sure that the powder storage chamber S1 and the liquid storage chamber S2 are interconnected.

The second detachable piece 44 is attached to the medicine bag 1 at a location to the right of the hanging hole 9. On the second detachable piece 44, there is provided a basic information indicating area E9 for indicating basic information like the indicating areas E1-E3.

According to the present embodiment, it is possible to tear off the first detachable piece 43 from the base part 12 from a left side by holding the tab portion 24 and then tear off the first detachable piece 43 from the second detachable piece 44 along the perforation 42.

Further, the second detachable piece 44 is configured such that the user can tear off the second detachable piece 44 from the base part 12 and attach the same to a patient's medical sheet or the like when recording how the medicine bag 1 was used, or how the medicine was administered to the patient, for instance. As the second detachable piece 44 is used in this way, it is possible to alleviate work load of a medical worker responsible for keeping a record of medicinal dosages and securely prevent such a problem that the administered medicine is wrongly recorded.

Figure 6:
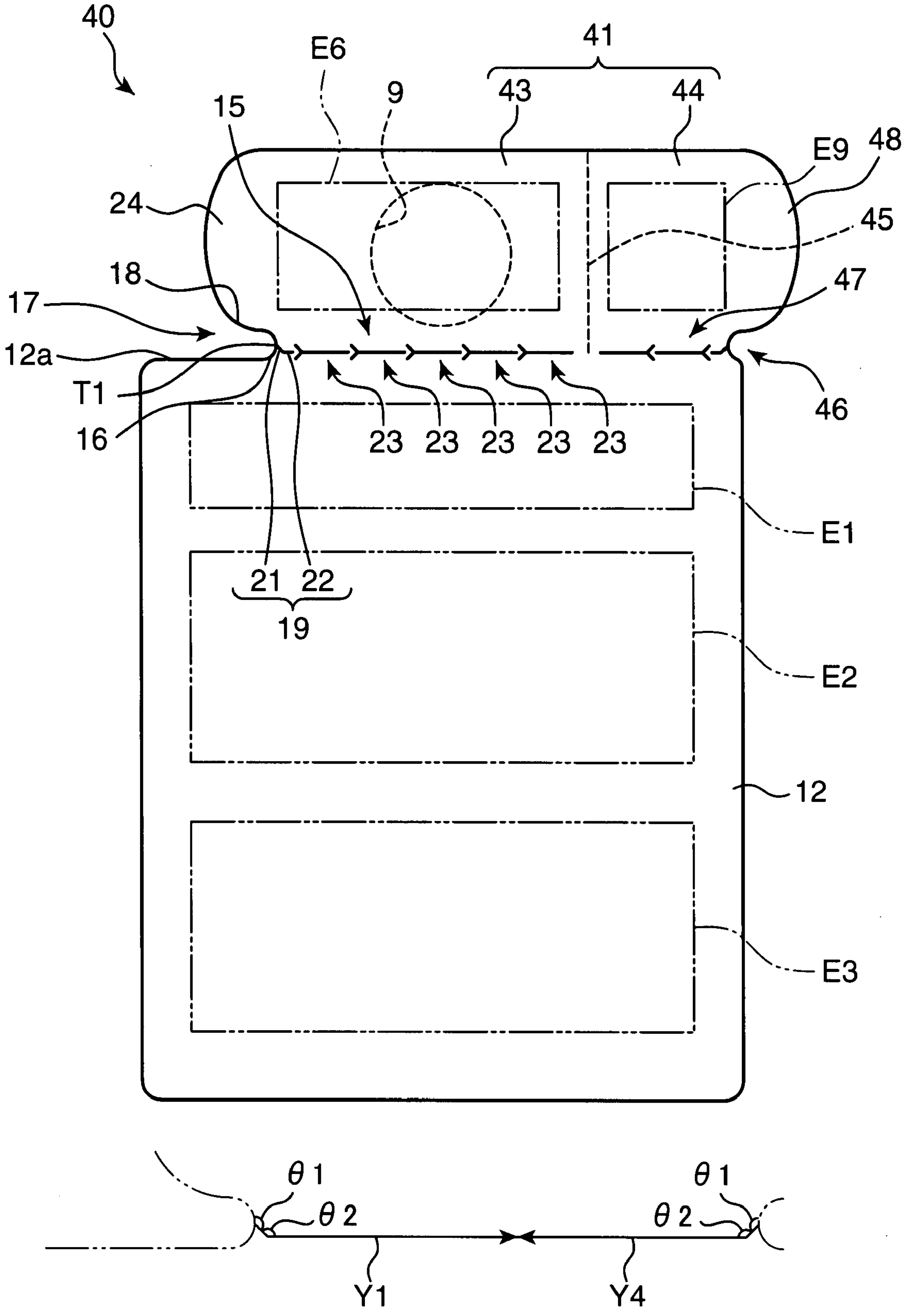
FIG. 6 is a developed plan view showing a label of which detachable part is divided into two pieces.

While the first detachable piece 43 and the second detachable piece 44 are joined to each other along the perforation 42 in the embodiment described above, these detachable pieces 43, 44 may be already separated by a slit 45 as shown in FIG. 6.

In a case where the individual detachable pieces 43, 44 are pre-separated as mentioned above, it is possible to define a tearing direction of the first detachable piece 43 and a tearing direction of the second detachable piece 44 in opposite directions left and right.

Specifically, in an embodiment shown in FIG. 6, there is also formed a recessed part 46 in a right edge portion of the base part 12 and the detachable part 41. This recessed part 46 is shaped left-right symmetrically with the recessed part 17 in plan view.

Then, there is formed a tear-off line 15 extending along the tearing direction Y1 in a range from the recessed part 17 to the slit 45, whereas there is formed a tear-off line 47 extending along a tearing direction Y4 left-right symmetrically with the tearing direction Y1 in a range from the recessed part 46 to the slit 45.

Furthermore, there is formed a rightward extending tab portion 48 on the second detachable piece 44 according to the present embodiment. This tab portion 48 is left-right symmetrically with the tab portion 24 of the first detachable piece 43.

Therefore, according to the present embodiment, the first detachable piece 43 can be torn off from the base part 12 by holding the tab portion 24 while the second detachable piece 44 can be torn off from the base part 12 by holding the tab portion 48.

The characteristic information indicated in the characteristic information indicating area E6 may take various forms depending on where the label 40 is attached to the medicine bag 1. Although the embodiment has illustrated an example in which the detachable part 14 is attached to cover the hanging hole 9, an area where the detachable part 14 is attached is not limited to this location but may be selected as shown in FIGS. 7 and 8.

Figure 7A:
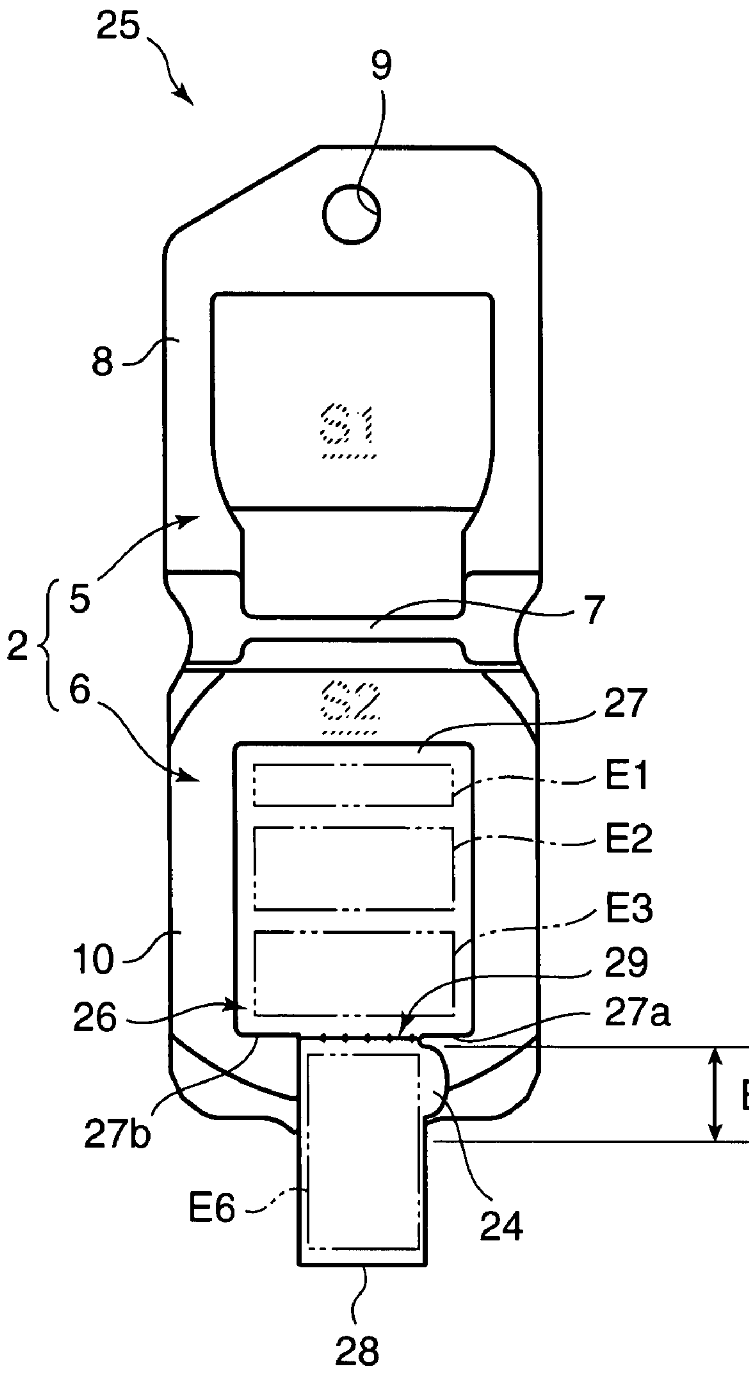
FIG. 7A is a plan view and FIG. 7B is a side view.
Figure 7B:
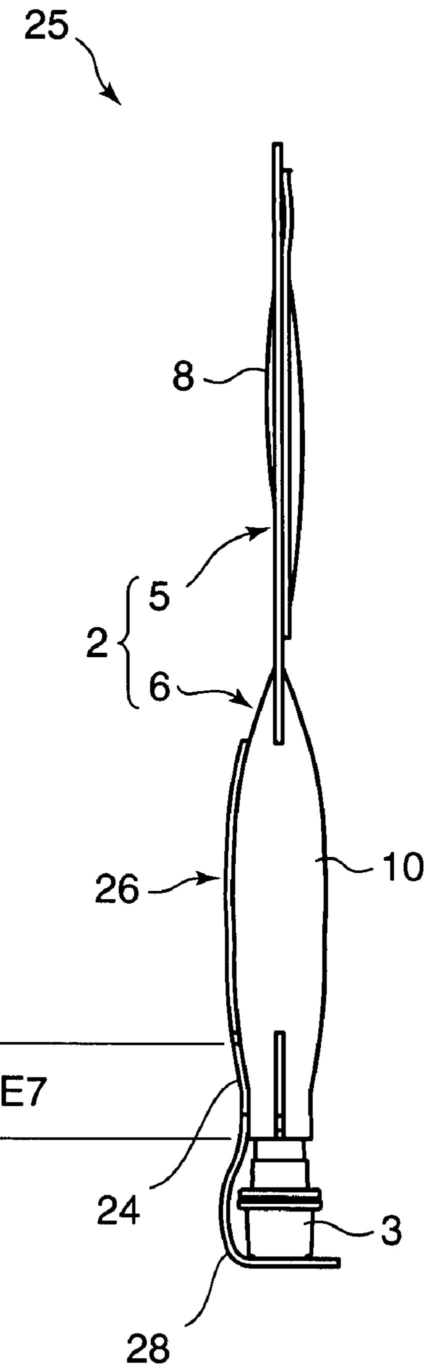

FIG. 7 shows a medicine bag according to another embodiment of the present invention, in which FIG. 7A is a plan view and FIG. 7B is a side view. FIG. 8 is an enlarged development view of a label of FIG. 7.

Figure 8:
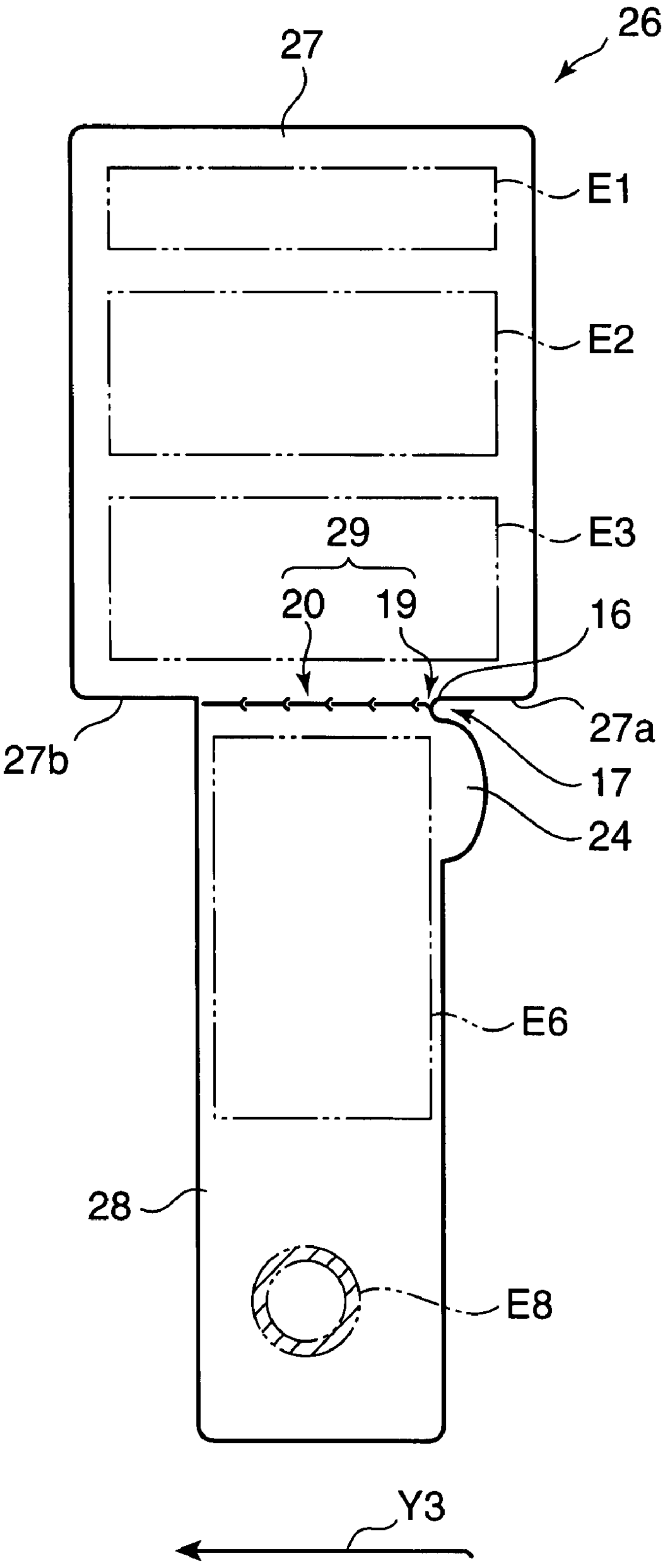
FIG. 8 is an enlarged development view of a label of FIG. 7.

Referring to FIGS. 7 and 8, the medicine bag 25 of this embodiment includes a container body 2, a port 3 and a label 26. Since the container body 2 and the port 3 are constructed similarly to the foregoing embodiments, elements like those of the foregoing embodiments are designated by the same symbols and a description of such elements is not provided in the present embodiment.

The label 26 includes a generally rectangular base part 27 and a detachable part 28 extending downward from the base part 27 by way of a left shoulder portion 27*a* and a right shoulder portion 27*b*. Between the base part 27 and the detachable part 28, there is formed a tear-off line 29 with a defined tearing direction Y3 (right to left as shown in the Figure).

Specifically, compared to the label 4 of the embodiment, the label 26 of the present embodiment is attached in a position vertically inverted with respect to the container body 2. For this reason, elements configured like those of the label 4 of the embodiment are designated by the same symbols and a description of such elements is omitted in the following discussion. Instead, elements configured differently from the label 4 are described in detail.

The base part 27 is attached to a front surface of the liquid container 6 by means of an adhesive layer formed over an almost entire rear surface area of the base part 27. On a front surface of the base part 27, there are provided the product name indicating area E1, the ingredients indicating area E2 and the lot number indicating area E3 in this order from an edge (top side) of the base part 27 opposite to the detachable part 28. Contents of indications on these indicating areas E1-E3 are the same as in the foregoing embodiments.

Extending downward from the base part 27, the detachable part 28 is configured to close off an opening in the port 3. Specifically, the detachable part 28 is attached to the liquid container 6 in an area below the base part 27 by an adhesive layer formed in top and bottom areas E7 of a rear surface of the detachable part 28. As in the embodiment, there is formed an area uncovered by the adhesive layer (refer to the hatched areas of FIG. 4) and a tab portion 24 is formed in the area uncovered by the adhesive layer.

A lower end portion of the detachable part 28 is folded back along a bottom end of the port 3 and peelably joined to the bottom surface of the port 3 in a joint area E8. An adhesive layer may be formed on the rear surface of the detachable part 28 in an area corresponding to this joint area E8 so that the detachable part 28 is attached to the port 3 by this adhesive layer.

On a front surface of the detachable part 28, there is provided the characteristic information indicating area E6 in an area to the front of the folded portion (closer to the base part 27). Information indicated in this characteristic information indicating area E6 is the same as in the foregoing embodiments.

In this embodiment, the detachable part 28 can be used also as a tamper seal, so that the user would peel off the detachable part 28 from the port 3 and attempt to tear off the detachable part 28 along the tear-off line 29 when inserting a needle through the port 3. At this time, the user would visually inspect the characteristic information indicating area E6 and recognize that the weak seal part 7 must be broken apart.

To summarize, according to the medicine bag 25 of the present embodiment, the detachable part 28 closes off the port 3 and, thus, it is possible to enable the user to recognize the characteristic information indicated on the detachable part 28 in a reliable fashion when the user is going to peel off the detachable part 28 to open the port 3 at the time of use of the medicine bag 25. This arrangement serves to prevent the user's failure to follow a correct operating procedure, for instance.

While the medicine bag 25 of the foregoing embodiment has been described with reference to an example in which the detachable part 28 is attached directly to the port 3, the detachable part 28 may be attached on top of a tamper seal 11 attached to the port 3.

Also, in the label 26 configured such that the detachable part 28 is attached to the port 3 or the tamper seal 11 as in the foregoing embodiment, it is preferable to form another tear-off line in the detachable part 28.

Figure 9:
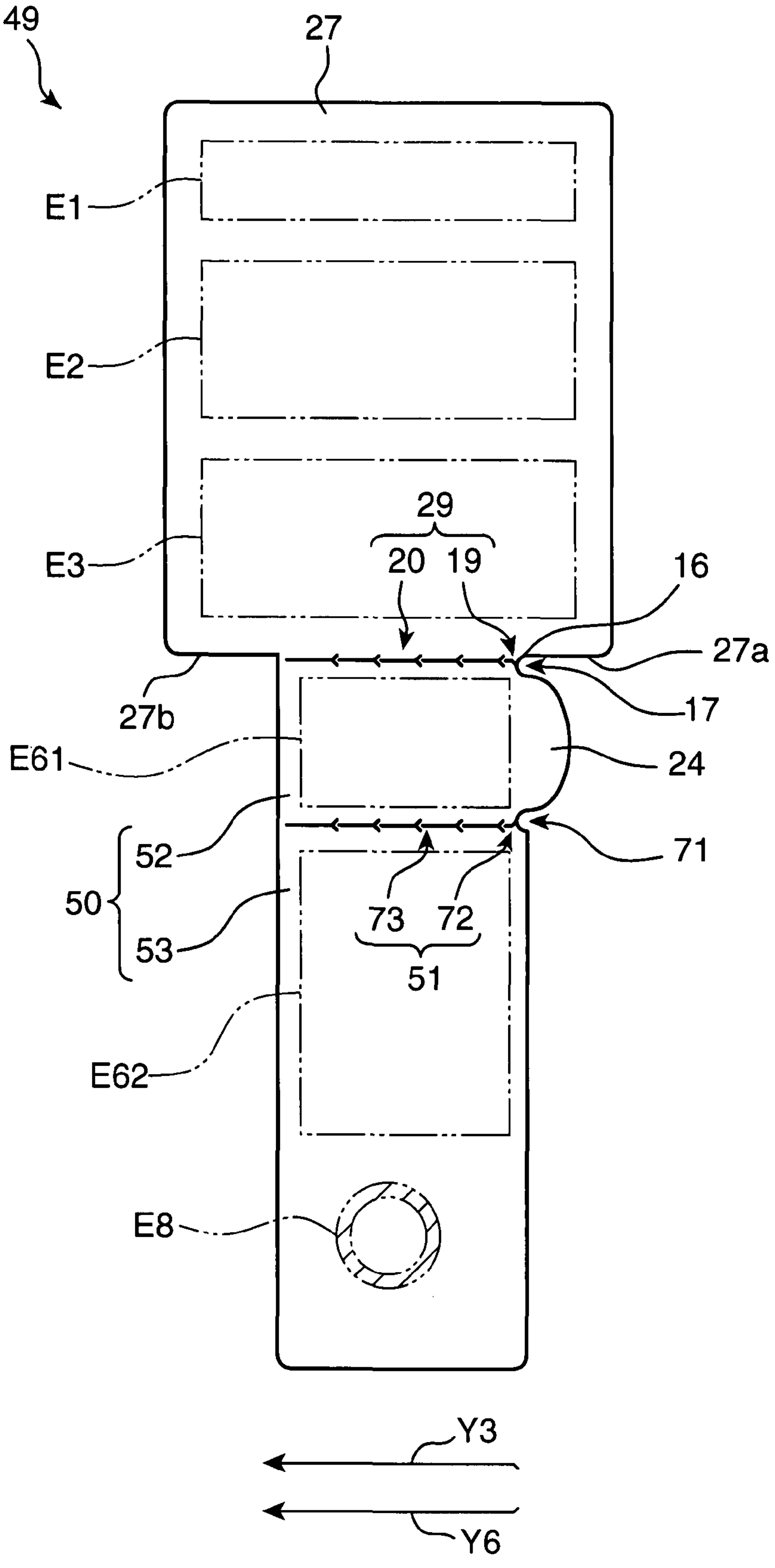
FIG. 9 is a developed plan view showing a label in which two tear-off lines are formed.

FIG. 9 is a plan view showing a label according to still another embodiment of the present invention.

Referring to FIG. 9, the label 49 of this embodiment includes the base part 27 and a detachable part 50 extending downward from the base part 27. Between the base part 27 and the detachable part 50, there are formed the tear-off line 29 and the recessed part 17.

In the detachable part 50 of this embodiment, there are formed a tear-off line 51 and a recessed part 71 in a tearing direction Y6 symmetrically with the tear-off line 29 with respect to a vertically center line passing the tab portion 24. This means that the tear-off line 51 and the tear-off line 29 are formed at upper and lower positions of a root portion of the tab portion 24. The tear-off line 51 is configured in a manner similar to the tear-off line 29 except that a start portion of the tearing direction Y6 is vertically inverted with respect to that of a tearing direction Y3 (which means that the tear-off line 51 is similarly configured except that a tearing slit 72 is vertically inverted with respect to the tearing slit 19).

Since the tear-off line 29 and the tear-off line 51 are formed at the upper and lower positions of the tab portion 24 and the respective tearing directions Y3 and Y6 are defined symmetrically up and down with the tab portion 24 located in between as mentioned above, a force applied to the tab portion 24 (or the force applied from right to left) is simultaneously transmitted to both end directions (upward and downward directions) of the tab portion 24.

Specifically, the force applied to the tab portion 24 is transmitted from an arc-shaped segment of the recessed part 17 through the tearing slit 19, and from the tearing slit 19 through the perforation 20, in two steps along gently changing directions. At the same time, the force applied to the tab portion 24 is transmitted from an arc-shaped segment of the recessed part 71 through the tearing slit 72, and from the tearing slit 72 through a perforation 73, in two steps along gently changing directions.

Also, the detachable part 50 includes a first connected section 52 detachably joined to the base part 27 along the tear-off line 29 and a second connected section 53 detachably joined to the first connected section 52 along the tear-off line 51.

There is provided a first characteristic information indicating area E61 on the first connected section 52, while there is provided a second characteristic information indicating area E62 on the second connected section 53 in an area to the front of a portion of the detachable part 50 (closer to the second connected section 53) folded back toward the port 3.

A joint area E8 in an extreme end portion of the second connected section 53 is joined to the port 3 or a rear surface of the extreme end portion of the second connected section 53 is joined to a tamper seal 11 (refer to FIG. 1).

According to the label 49 of the present embodiment, the second connected section 53 attached to the port 3 or the tamper seal 11 is joined to the base part 27 via the first connected section 52, so that the user who is going to use the container body 2 to which this label 49 is attached is required to peel off the second connected section 53 from the container body 2 upon separating the base part 27 and the second connected section 53 from each other by tearing off the first connected section 52 from the base part 27 and the second connected section 53 at first.

Therefore, according to this embodiment, it is possible to have the user concentrate more attention on the detachable part 50 by as much as an increase in the amount of preparatory work to be done for using the container body 2.

Particularly if the first characteristic information indicating area E61 and the second characteristic information indicating area E62 are configured to indicate different kinds of characteristic information, such as an instruction that use of any medicine in the container body 2 for injection purposes must be prohibited and an instruction that infusion must be commenced after the medicine in the powder storage chamber S1 has been dissolved in the medicine in the liquid storage chamber S2, it is possible to enable the user to recognize these pieces of information in a reliable fashion.

Figure 10:
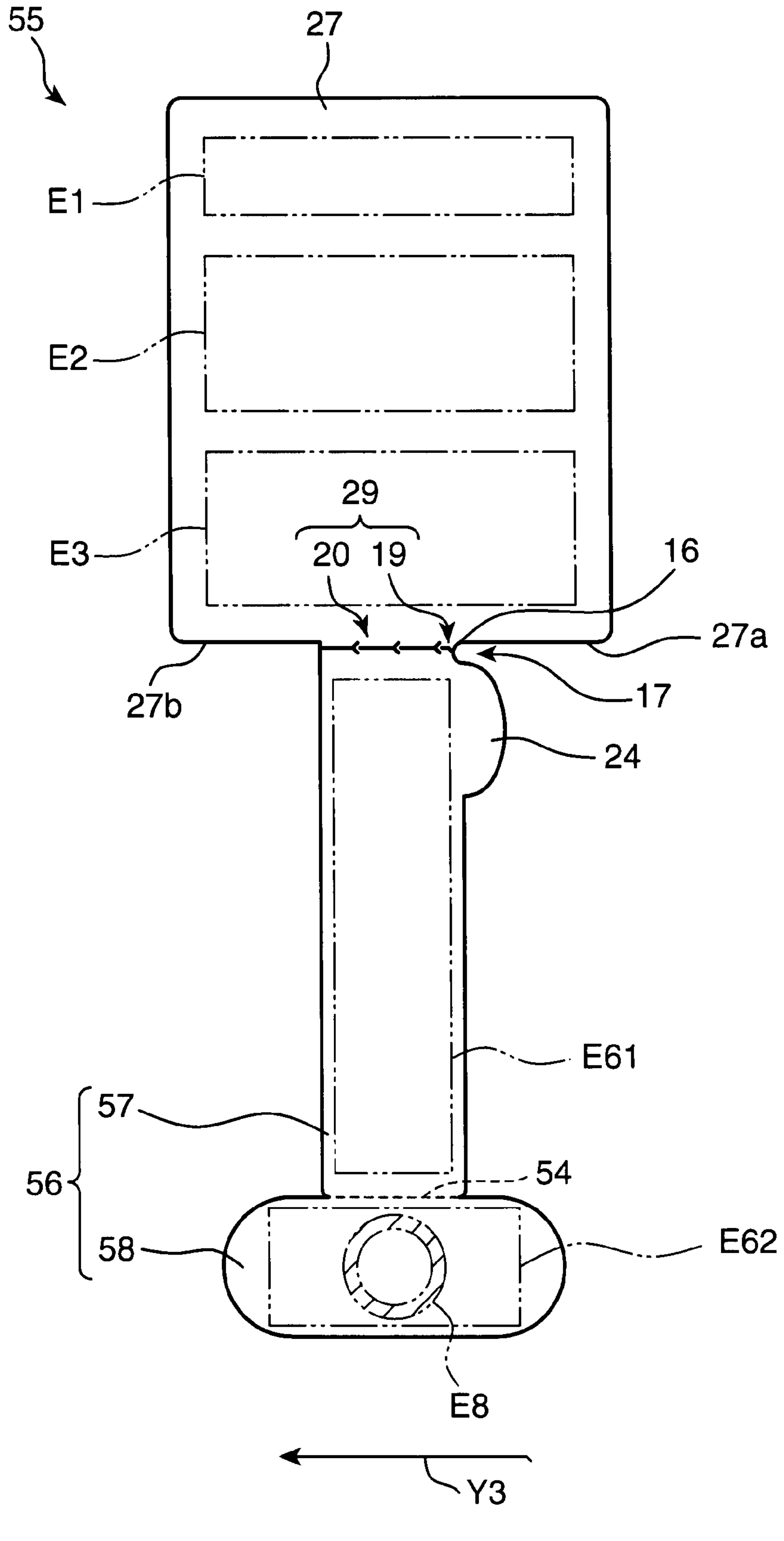
FIG. 10 is a developed plan view showing a label in which the location of a tear-off line is varied.

Also, while the tear-off line 51 is provided at a location where the tab portion 24 is sandwiched between the tear-off line 29 and the tear-off line 51 in the embodiment, a perforation 54 may be formed in the vicinity of a joint area where a label is joined to the port 3 or the tamper seal 11 as shown in FIG. 10.

Specifically, the label 55 according to an embodiment of FIG. 10 includes the base part 27 and a detachable part 56 extending downward from the base part 27. Between the base part 27 and the detachable part 56, there are formed the tear-off line 29 and the recessed part 17 (refer to FIG. 8).

The detachable part 56 includes a first connected section 57 extending from the base part 27 and a second connected section 58 formed at an extreme end (lower end) of this first connected section 57, wherein the first connected section 57 and the second connected section 58 are made splittable from each other along the perforation 54 extending along a left-to-right direction.

There is provided the first characteristic information indicating area E61 on the first connected section 57, while there is provided the second characteristic information indicating area E62 on the second connected section 58. This means that the first characteristic information indicating area E61 is disposed on a front side of the container body 2 and the second characteristic information indicating area E62 is disposed on a bottom side of the container body 2 in a state in which the label 55 is attached to the container body 2.

When using the container body 2 to which the label 55 of this embodiment is attached, the user separates the base part 27 and the second connected section 58 from each other by tearing off the first connected section 57 from the base part 27 and the second connected section 58 at first.

Subsequently, the user peels off the second connected section 58 from the port 3 or the tamper seal 11 (refer to FIG. 1) to which the second connected section 58 is left attached.

When the user is going to use the container body 2 to which the label 55 is attached, the user's attention is drawn to the first connected section 57 at first so that the user will recognize information indicated in the first characteristic information indicating area E61 provided on the first connected section 57 and, then, the user's attention is drawn to the second connected section 58 which is left on the side of the port 3 so that the user will recognize information indicated in the second characteristic information indicating area E62 provided on the second connected section 58.

Figure 11:
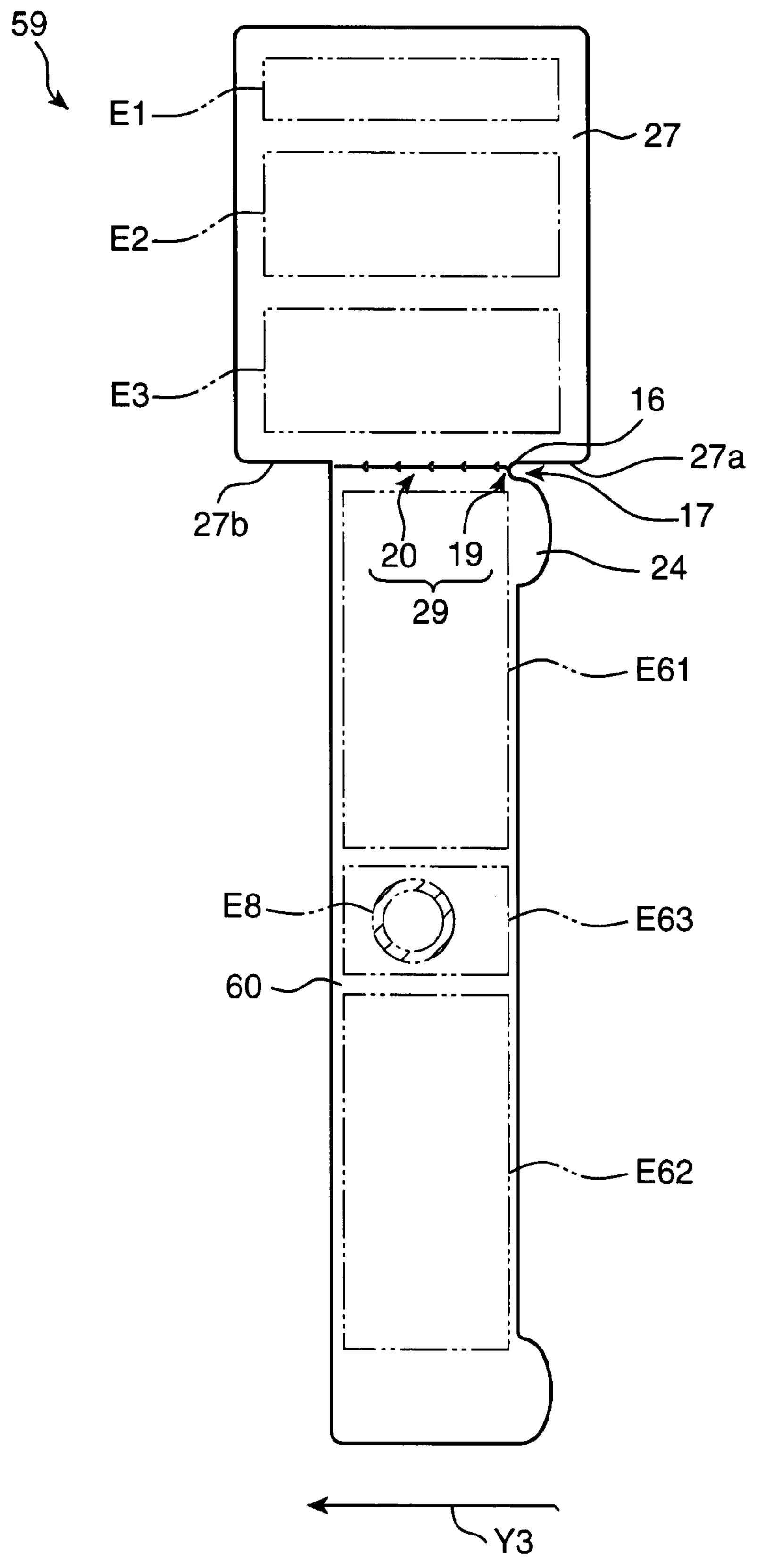
FIG. 11 is a developed plan view showing still another embodiment of the present invention.
Figure 12:
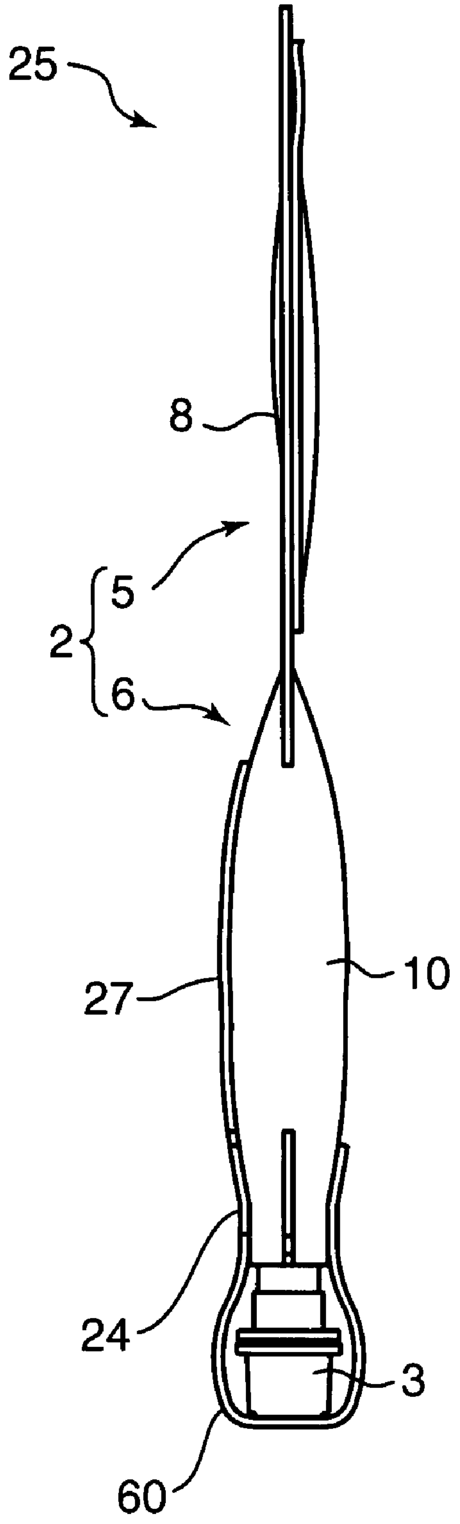
FIG. 12 is a side view showing a state in which a label of FIG. 11 is attached to a container body.

While the foregoing individual embodiments have been described with reference to a construction in which the base part 27 is attached to the front surface of the container body 2 and an extreme end (lower end) of the detachable part 28, 50, 56 is attached to the port 3 or the tamper seal 11, it is possible to attach the detachable part to both the front and rear surfaces of the container body 2 as shown in FIG. 12 by using a label 59 shown in FIG. 11.

Referring to FIGS. 11 and 12, the label 59 according to the present embodiment includes the base part 27 and a detachable part 60 extending downward from the base part 27. Between the base part 27 and the detachable part 60, there are formed the tear-off line 29 and the recessed part 17.

The detachable part 60 according to the present embodiment is configured such that an approximately central area of the detachable part 60 along a longitudinal direction thereof is attached to the port 3 or the tamper seal 11 (refer to FIG. 1).

Specifically, the detachable part 60 is configured to have such a length that the detachable part 60 can be attached to the container body 2 from the front surface to the rear surface thereof, straddling the port 3, so that a middle portion of the detachable part 60 can be attached to the bottom surface of the port 3 or the tamper seal 11 (refer to FIG. 1) as shown in FIG. 12.

On the detachable part 60, there are formed the first characteristic information indicating area E61 and the second characteristic information indicating area E62 on both sides of the portion attached to the port 3 or the tamper seal 11.

When using the container body 2 to which the label 59 thus configured is attached, the user peels off an extreme end portion of the detachable part 60 from the rear surface of the container body 2 and, then, tears apart the detachable part 60 and the base part 27 along the tear-off line 29 on the front surface side of the container body 2.

When the user is going to use the container body 2 to which the label 59 is attached, the user's attention is drawn to the extreme end portion of the detachable part 60 attached to the rear surface of the container body 2 at first so that the user will recognize information indicated in the second characteristic information indicating area E62 provided in the extreme end portion of the detachable part 60. Subsequently, the user's attention is drawn to the tear-off line 29 where the base part 27 and the detachable part 60 attached to the front surface of the container body 2 are torn apart so that the user will recognize information indicated in the first characteristic information indicating area E61 provided in a basal portion of the detachable part.

Then, as the detachable part 60 is peeled off from the port 3 or the tamper seal 11, the container body 2 becomes ready to be used.

Additionally, there may be provided a third characteristic information indicating area E63 between the two characteristic information indicating areas E61, E62 as shown in FIG. 11.

This configuration will make it possible to have the user further recognize information indicated in the third characteristic information indicating area E63 when peeling off the detachable part 60 from the port 3 or the tamper seal 11.

Figure 13:
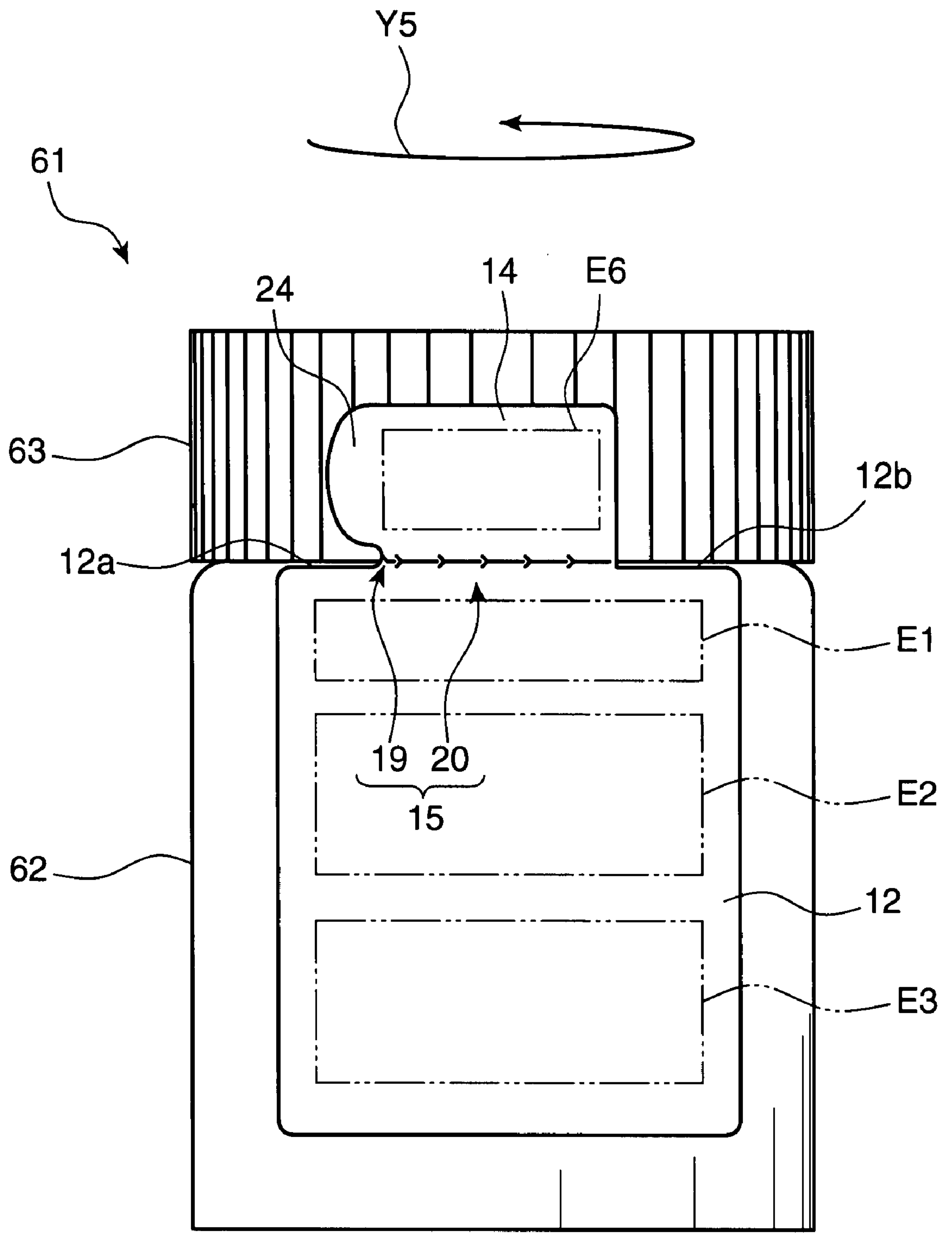
FIG. 13 is a front view showing a state in which the label of FIG. 1 is attached to a capped container.

While the labels to be attached to the medicine bags have been described in the foregoing embodiments, the label may be attached to a capped container (storage container) 61 shown in FIG. 13. Described hereinbelow is an example in which the label 4 of the embodiment is attached to the capped container 61.

Referring to FIG. 13, the capped container 61 includes a container body 62 and a cap 63 which is placed on top of the container body 62 and screwed thereon for closing off the container body 62.

The label 4 is attached in a state in which the label 4 straddles the container body 62 and the cap 63 with the tearing direction Y2 of the perforation 20 aligned with a lower edge of the cap 63.

As the user turns the cap 63 in an opening direction Y4 thereof relative to the container body 62 when removing the cap 63 from the container body 62, the label 4 is torn apart into the base part 12 and the detachable part 14 along the tear-off line 15.

Therefore, if the label 4 is attached to the capped container 61, it is possible to judge whether the capped container 61 has already been opened by inspecting whether the detachable part 14 has been torn apart from the base part 12 or not.

Figure 14B:
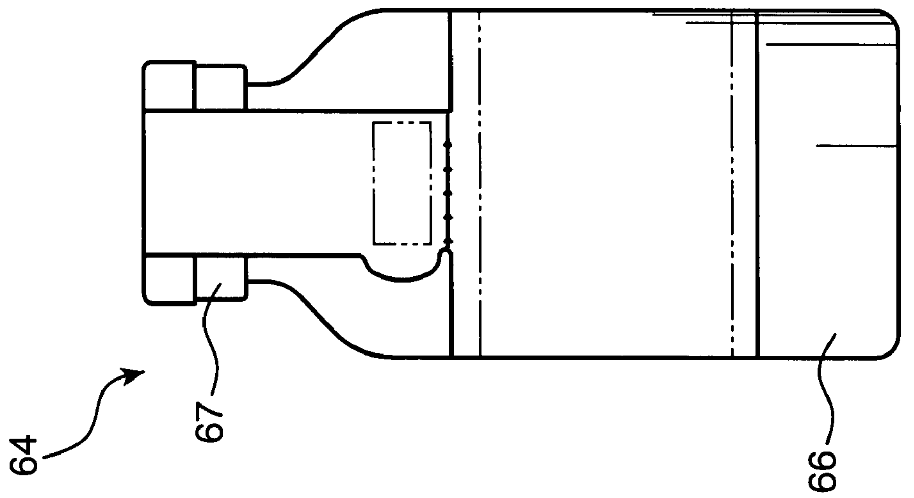
FIG. 14A is a diagram showing a developed state of the label and FIG. 14B is a diagram showing a state in which the label is attached to a vial.
Figure 14A:
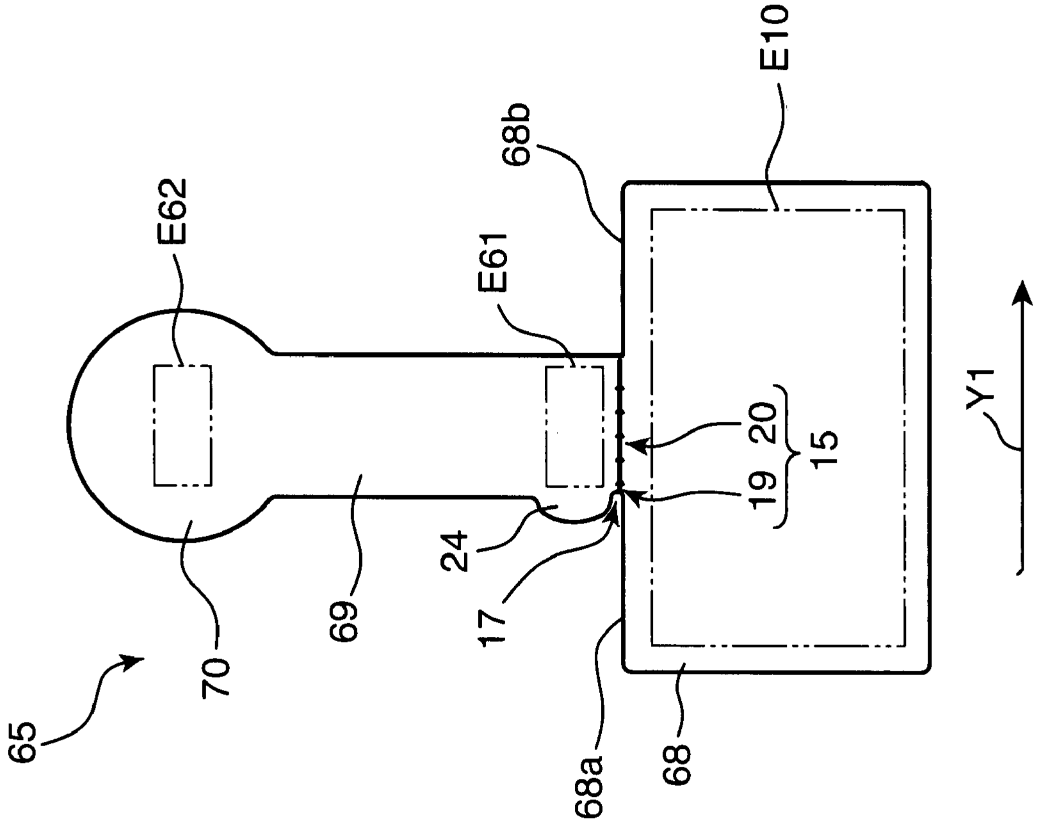

It is also possible to provide a label 65 suited to a vial 64 as shown in FIG. 14B.

The vial 64 according to the present embodiment includes a reagent bottle 66 and a cap 67 for closing off the reagent bottle 66. The vial 64 is configured such that a medicine in the reagent bottle 66 can be drawn by piercing a rubber plug fitted in the cap 67 with an unillustrated syringe needle and the reagent bottle 66 can be closed off again by extracting the syringe needle.

The label 65 includes a generally rectangular base part 68 and a detachable part 69 extending upward from the base part 68 by way of a left shoulder portion 68*a* and a right shoulder portion 68*b*. Between the base part 68 and the detachable part 69, there are formed the tear-off line 15 and the recessed part 17 (refer to FIG. 1).

On the base part 68, there is provided a basic information indicating area E10 for indicating the basic information.

On the detachable part 69, there are formed the tab portion 24 on a left side of a basal portion of the detachable part 69 and a generally circular protective portion 70 at an extreme end of the detachable part 69.

The protective portion 70 is attached to the rubber plug in the cap 67 of the vial 64 or to a cap covering the rubber plug to prevent the rubber plug from being pierced by an unillustrated syringe needle.

On the detachable part 69, there are also provided a first characteristic information indicating area E61 at a location in the vicinity of the tab portion 24 and a second characteristic information indicating area E62 in the protective portion 70.

When using the vial 64 to which the label 65 thus configured is attached, the user will notice that the rubber plug in the cap 67 is covered by the protective portion 70 and recognize information indicated in the second characteristic information indicating area E62 provided in the protective portion 70.

Subsequently, the user will attempt to tear apart the detachable part 69 and the base part 68 by holding the tab portion 24. At this time, the user will recognize information indicated in the first characteristic information indicating area E61 provided in the vicinity of the tab portion 24.

Since the protective portion 70 can be attached at a location where the use of the vial 64 is hindered according to the label 65 as described above, it is possible to have the user recognize the information indicated in the first characteristic information indicating area E61 and the second characteristic information indicating area E62.

While the foregoing individual embodiments have illustrated the medicine bags 1 and 25, by way of example, in which the powder medicine and the liquid medicine are accommodated in the respective storage chamber S1 and S2, the medicine bags 1 and 25 may be so configured as to accommodate liquid medicines in both of the individual storage chamber S1 and S2.

Figure 15:
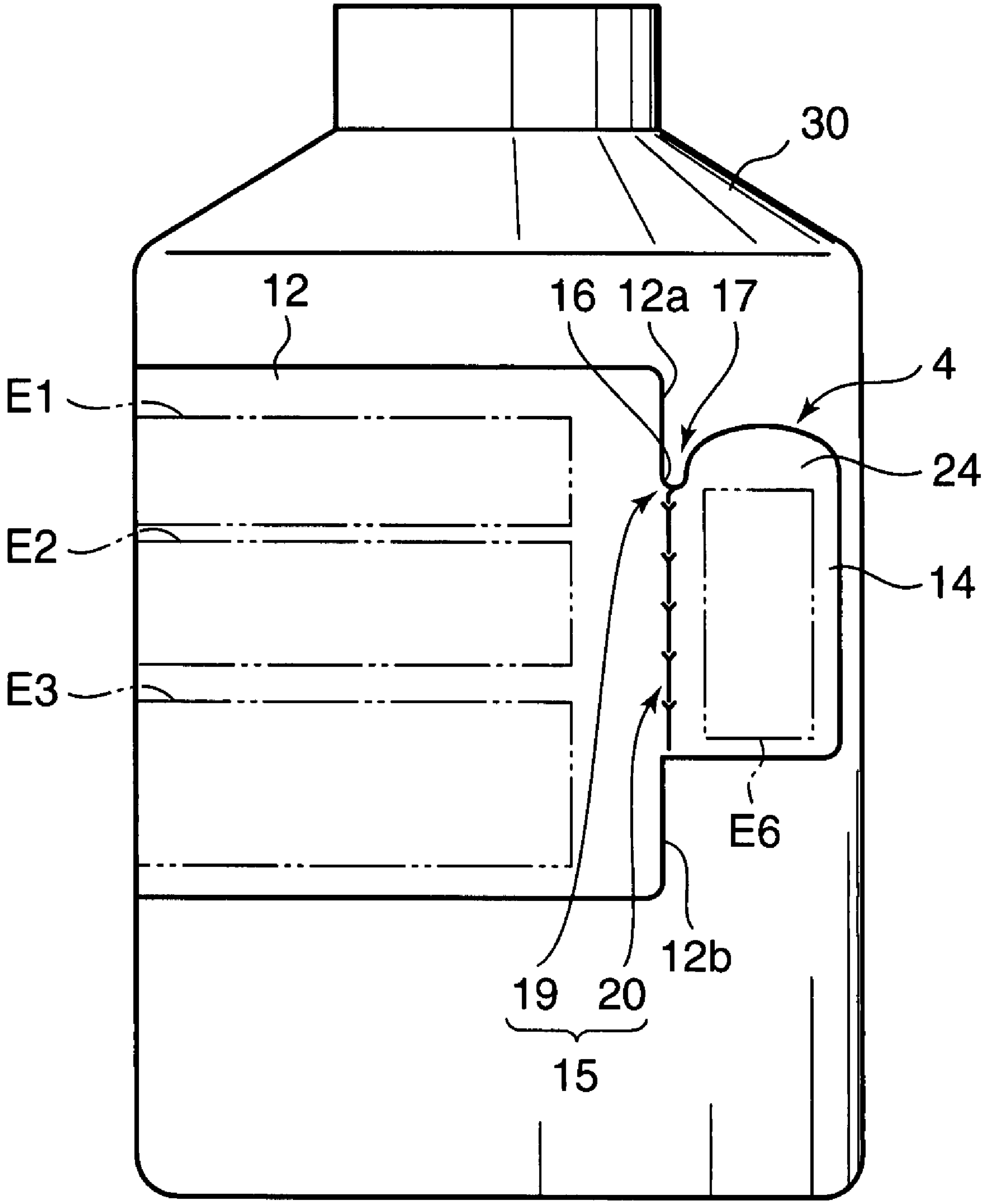
FIG. 15 is a front view showing another state in which the label of FIG. 1 is used.

Furthermore, the labels 4, 26 and 40 of the foregoing individual embodiments may be attached to a medicine bottle 30 accommodating a specific medicine to wrap around the same as shown in FIG. 15. (Disclosed in FIG. 15 is the label 4.) In this case, it is preferable to indicate in the characteristic information indicating area E6 on the detachable part 14 such information that makes it possible to selectively specify contents indicated in the individual indicating areas E1-E3 on the base part 12.

This arrangement makes it possible to securely keep a clinical record of a patient on the patient's medical sheet by tearing off the detachable part 14 from the base part 12 and attaching the same to the medical sheet upon administering the medicine accommodated in the medicine bottle 30 to the patient.

Since the label 4 is used in a position oriented in a horizontal direction of the medicine bottle 30 as shown in FIG. 15, the indicating areas E1-E3 are vertically laid out. In a case where the label 4 is attached to the medicine bottle 30, the characteristic information need not necessarily be indicated in the detachable part 14.

Also, while the foregoing individual embodiments have described examples in which the bottom portion 16 has generally a semicircular shape, the bottom portion 16 should at least have a rounded shape. For example, the bottom portion 16 may be formed into a quadrant shape.

Furthermore, while the tearing slit 19 is formed into a shape having the introductory portion 21 and the bent portion 22 in the foregoing individual embodiments, it is possible to form the tearing slit 19 itself into a curved shape. In this case, it is preferable that an opening angle of the curved shape (or an angle corresponding to the angle θ2) be made an obtuse angle.

Also, while the foregoing individual embodiments have described examples in which the indicating areas E1-E3 indicate pieces of information corresponding to the respective indicating areas E1-E3, combinations of these indicating areas E1-E3 and the pieces of information indicated therein are not particularly limited but may be altered as appropriate. In the medicine bag 1 of this invention, the basic information should at least be indicated in the base part 12 or 17.

Furthermore, while the foregoing individual embodiments have described constructions having the Y-shaped slits 23, the slits 23 are not limited to the Y-shape but may be formed into a linear shape (which is the shape of the leg portions 23*a* of the foregoing embodiments), for example.

Also, while the foregoing individual embodiments have described constructions in which the tearing slit 19 extends from the bottommost point T1 of the bottom portion 16, the tearing slit 19 need not necessarily extend from the bottommost point. A construction in which the tearing slit 19 extends from the proximity of the bottommost point T1 can produce the same advantageous effect as the foregoing individual embodiments.

According to the labels 4, 26 and 40 of the foregoing individual embodiments, the tearing slit 19 is so formed as to intersect the bottom portion 16 of the recessed part 17. Thus, it is possible to transmit a force applied to the detachable part 14, 28 or 41 along the edge of the detachable part 14, 28 or 41 forming the recessed part 17 and redirect the force from the bottom portion 16 of the detachable part 14, 28 or 41 into the intersecting direction, so that the force is transmitted to the tearing slit 19. Therefore, according to the labels 4, 26 and 40, the force applied to the detachable part 14, 28 or 41 can be efficiently transmitted to the tearing slit 19 as a force acting along the tearing direction Y1, so that the base part 12 and the detachable part 14, 28 or 41 can easily be torn apart.

One possible approach to efficiently transmitting the force applied to the detachable part 14, 28 or 41 might be to form the tearing slit 19 on an extended line of the edge of the detachable part 14, 28 or 41 constituting the curved portion 18 of the recessed part 17 (or the portion located more outward than the bottom portion 16). This approach however has had a problem that the force applied to the detachable part 14, 28 or 41 would not be transmitted to the tearing slit 19 but toward the bottom portion 16 in a boundary area between the curved portion 18 and the bottom portion 16, thereby producing a problem that the base part 12 and the detachable part 14, 28 or 41 would be torn apart from the bottom portion 16.

Conversely, another possible approach might be to form the tearing slit 19 on an extended line of the shoulder portion 12*a* of the base part 12 or 27 constituting one side of the recessed part 17. In this case, however, there is a likelihood that the force applied to the detachable part 14, 28 or 41 acts as a force which tears apart the label 4, 26 or 40 at the bottom portion before the force reaches a boundary area between the shoulder portion 12*a* and the bottom portion 16.

In the labels 4, 26 and 40, the tearing slit 19 is so formed as to intersect the bottom portion 16 of the recessed part 17, so that the force applied to the detachable part 14, 28 or 41 can be efficiently transmitted to the tearing slit 19 as a force acting along the tearing direction Y1 and, as a consequence, the base part 12 or 27 and the detachable part 14, 28 or 41 can easily be torn apart.

Specifically, the present invention discussed in the foregoing embodiments provides a label to be attached to a medicine bag accommodating medicines, the label including a base part indicating thereon basic information including at least information on ingredients of the medicines accommodated in the medicine bag, and a detachable part detachably joined to the base part, the label being characterized in that the detachable part is so shaped as to be attachable to such an area of the medicine bag that it becomes difficult to use the medicine bag when a surface of the area is covered, and the detachable part indicates thereon characteristic information including at least directions on use of the medicine bag.

According to the label of this invention, the characteristic information is indicated on the separately formed detachable part. This layout on the label not only allows for differentiation between the characteristic information and the basic information indicated on the base part but enables the user to recognize the characteristic information in a reliable fashion because the detachable part can be attached to such an area of the medicine bag that the detachable part attached thereto would hinder the use of the medicine bag.

Specifically, when using the medicine bag, the user would tear off the detachable part attached to the area from the base part. It is possible to enable the user to visually recognize the characteristic information at this time, since the characteristic information is indicated on the detachable part.

Therefore, according to the label of the present invention, it is possible to enable the user to securely recognize the characteristic information which is necessary when using the medicine bag.

In the label, it is preferable that the base part and the detachable part be made tearable apart along a tear-off line having a defined tearing direction, and there be formed a tab portion in the detachable part by not providing an adhesive layer on a rear surface of the detachable part at an upstream end of the tearing direction.

According to this construction, the tearing direction is limited to one direction along the tear-off line and the tab portion is formed at the upstream end of the tearing direction, so that the user can easily tear off the detachable part from the base part by holding the tab portion.

In the label, it is preferable that there be formed a recessed part having a rounded bottom portion in an edge portion of the base part and the detachable part, the bottom portion extending along both of the base part and the detachable part, and the tear-off line include a tearing slit which makes the edge portion of the base part and the detachable part tearable from each other at the upstream end of the tearing direction and a perforation located downstream of the tearing slit along the tearing direction, wherein the tearing slit is so arranged as to be oriented in a direction intersecting the bottom portion of the recessed part.

According to this construction, the tearing slit is formed along the direction intersecting the bottom portion of the recessed part (toward the direction intersecting the bottom portion of the recessed part). Thus, it is possible to transmit a force applied to the tab portion along the edge portion of the detachable part forming the recessed part and redirect the force from the bottom portion of the recessed part into the intersecting direction, so that the force is transmitted to the tearing slit. Therefore, according to this construction, the force applied to the detachable part can be efficiently transmitted to the tearing slit as a force acting along the tearing direction, so that the base part and the detachable part can easily be torn apart.

Here, the expression concerning the tearing slit that "makes the edge portion of the base part and the detachable part tearable apart" refers not only to an arrangement in which the edge portion of the base part and the detachable part is already torn apart over a specified range but also to an arrangement in which a slit passing through the base part and the detachable part in a thickness direction thereof is formed at a downstream position of the tearing direction at an extremely small distance from the edge portion of the base part and the detachable part. In other words, the expression includes an arrangement in which the slit is formed to allow the base part and the detachable part to be torn apart by as much as the extremely small distance when a specific force is applied to the tab portion.

Also, the expression "the direction intersecting the bottom portion of the recessed part" refers to a direction other than a tangential direction of the bottom portion having a rounded shape, wherein the direction along the tearing slit intersects the bottom portion at a specific angle.

In the label, it is preferable that the perforation be laid out closer to the base part than the tearing slit, the tearing slit extend in the direction intersecting the bottom portion in the proximity of a bottommost point thereof so that an angle formed between the tearing slit and the bottom portion, opening toward the detachable part, becomes an obtuse angle, and the tearing slit be shaped to further extend, also forming an obtuse angle with the tearing direction along the perforation.

According to this construction, a tearing start point of the tearing slit and the perforation are vertically offset and the tearing slit forms obtuse angles with both the rounded bottom portion and the tearing direction along the perforation, so that a force applied to the tab portion can be smoothly transmitted all the way along an edge of the detachable part forming the recessed part, the tearing slit and the perforation in this order. Therefore, according to the construction, it is possible to prevent such a problem that a portion other than the tear-off line breaks in an initial stage of lifting the tab portion.

One possible approach to allowing the detachable part to be neatly torn off from the base part might be to form a recessed part having a pointed bottom (such as a V-shaped recessed part) in an edge portion of the base part and the detachable part and to arrange the tear-off line to extend from this edge portion. Practically, however, it is difficult to form an acutely pointed part corresponding to the recessed part in a label-making cutting tool. Therefore, in a strict sense, the bottom portion of the recessed part is rounded in shape.

If the bottom portion of the recessed part is formed into a rounded shape and the tear-off line is formed at right angles to the rounded shape at the bottommost point thereof, the force applied to the tab portion will be redirected by approximately 90 degrees at the tear-off line after the force has been transmitted halfway along an arc-shaped segment of the rounded shape. Consequently, there arises a possibility that a portion other than the tear-off line may break when the force applied to the tab portion is redirected.

Since the tearing start point (which is in the proximity of the bottommost point of the bottom portion) and the perforation are vertically offset and there is provided the tearing slit interconnecting both along a gentle slope in the construction, the force applied to the tab portion is transmitted from the arc-shaped segment of the bottom portion through the tearing slit, and from the tearing slit through the perforation, in two steps along gently changing directions.

Thus, according to the construction, the tearing slit formed along the direction interconnecting the bottom portion in the proximity of the bottommost point thereof (in the direction interconnecting the bottom portion in the proximity of the bottommost point thereof) forms obtuse angles with the bottom portion and the tearing direction along the perforation. It is therefore possible to prevent breakage of other portions of the label than the tear-off line when the base part and the detachable part are detached from each other.

In the label, it is preferable that the tearing slit include an introductory portion which intersects the bottom portion at an obtuse angle and a bent portion which bends away from the introductory portion at an obtuse angle and is arranged on a line extended in the tearing direction along the perforation.

According to this construction, it is possible to transmit the force applied to the tab portion to the perforation in a reliable fashion by the introductory portion and the bent portion of the tearing slit.

It is preferable that the detachable part include a first detachable piece and a second detachable piece which are joined splittably from each other along a second tear-off line having a defined tearing direction intersecting the tearing direction between the base part and the detachable part, and the first detachable piece be configured to be attachable to such an area of the medicine bag that it becomes difficult to use the medicine bag when a surface of the area is covered.

According to this construction, it is possible to bring the medicine bag into a usable condition by peeling off the first detachable piece constituting part of the detachable part. On the other hand, the second detachable piece, can be left attached to the medicine bag even in this condition. Accordingly, by indicating the characteristic information on the second detachable piece, for instance, it is possible to continuously indicate the characteristic information to the user even after the first detachable piece has been peeled off.

The label may also be constructed such that the detachable part includes a first detachable piece and a second detachable piece which are already separated by a slit extending along a direction intersecting the tearing direction, the first detachable piece is configured to be attachable to such an area of the medicine bag that it becomes difficult to use the medicine bag when a surface of the area is covered, the recessed part and the tearing slit are formed in each of opposite edge portions of the base part and the detachable part, and opposite tearing directions are defined on the tear-off line in a range from one of these recessed parts to the slit and in a range from the other of these recessed parts to the slit.

This construction can also allow the user to continuously recognize the information indicated on the second detachable piece after the first detachable piece has been peeled off.

Furthermore, since the opposite tearing directions are defined on the tear-off line on opposite sides of the slit in this construction, the user can tear off the first detachable piece from one edge portion of the label and the second detachable piece from the other edge portion. Accordingly, compared to a case in which the user tears off the second detachable piece in the same direction after tearing off the first detachable piece, this construction can improve operability of the label as the second detachable piece can be torn apart from the side where the recessed part is formed.

If the label is constructed such that the second detachable piece indicates the characteristic information, the user may tear off the second detachable piece and attach the same to a patient's medical sheet or the like when recording that the medicine of the medicine bag was administered to the patient. This construction serves to alleviate a medical worker's work load needed for keeping a clinical record.

In the label, it is preferable that the detachable part include a first connected section detachably joined to the base part and a second connected section detachably joined to the first connected section, and the second connected section be configured to be attachable to such an area of the medicine bag that it becomes difficult to use the medicine bag when a surface of the area is covered.

According to this construction, the second connected section attached to such an area that it becomes difficult to use the medicine bag is joined to the base part via the first connected section, so that the user who is going to use the medicine bag to which this label is attached is required to peel off the second connected section from the medicine bag upon separating the base part and the second connected section from each other by tearing off the first connected section from the base part and the second connected section at first.

Therefore, according to this construction, it is possible to have the user concentrate more attention on the detachable part by as much as an increase in the amount of preparatory work to be done for using the medicine bag.

Particularly if the first connected section and the second connected section are configured to individually indicate the characteristic information, it is possible to enable the user to recognize the characteristic information in a reliable fashion by using the first connected section and the second connected section on which the user's attention is concentrated in a stage of the preparatory work.

Also, it is preferable that the characteristic information include at least one of such pieces of information that use of the medicines in the medicine bag for injection purposes must be prohibited and the medicine bag must be used after two kinds of medicines accommodated in the medicine bag have been mixed.

By displaying such pieces of information, it becomes possible to indicate to the user how to use the medicine bag and what is prohibited when using the same.

Also, the present invention discussed in the foregoing embodiments provides a medicine bag including the label, a container body accommodating medicines in an internal space thereof, the container body having a hanging hole formed in one end, and a port formed at the other end of the container body, the medicine bag being characterized in that the detachable part of the label is so attached as to cover at least part of the hanging hole, and the medicines in the container body are discharged through the port under conditions where the container body is suspended by the hanging hole.

According to the medicine bag of this invention, the detachable part closes off the hanging hole and, thus, it is possible to enable the user to recognize the characteristic information indicated on the detachable part in a reliable fashion when the user is going to peel off the detachable part to open the hanging hole at the time of use of the medicine bag. This arrangement serves to prevent the user's failure to follow a correct operating procedure, for instance.

Further, the present invention discussed in the foregoing embodiments provides a medicine bag including the label, a container body accommodating medicines in an internal space thereof, the container body having a hanging hole formed in one end, and a port formed at the other end of the container body, the medicine bag being characterized in that the detachable part of the label is so attached as to cover at least part of the port, and the medicines in the container body are discharged through the port under conditions where the container body is suspended by the hanging hole.

According to the medicine bag of this invention, the detachable part closes off the port and, thus, it is possible to enable the user to recognize the characteristic information indicated on the detachable part in a reliable fashion when the user is going to peel off the detachable part to open the port at the time of use of the medicine bag. This arrangement serves to prevent the user's failure to follow a correct operating procedure, for instance.

In the medicine bag, it is preferable that the base part of the label be attached to a front surface of the container body, a middle portion of the detachable part of the label be attached to the port, and an extreme end portion of the detachable part be attached to a rear surface of the container body.

According to this construction, the detachable part can be attached to the container body, straddling both front and rear surfaces thereof, so that the characteristic information can indicated on both the front and rear surfaces of the container body. This construction enables the user to recognize the characteristic information in a more reliable fashion.

Also, the present invention discussed in the foregoing embodiments provides a label to be attached to a specific object, the label including a base part, and a detachable part detachably joined to the base part along a tear-off line having a defined tearing direction, the label being characterized in that there is formed a recessed part having a rounded bottom portion in an edge portion of the base part and the detachable part, the bottom portion extending along both of the base part and the detachable part, and the tear-off line includes a tearing slit which makes the edge portion of the base part and the detachable part tearable from each other at an upstream end of the tearing direction and a perforation located downstream of the tearing slit along the tearing direction, wherein the tearing slit is so arranged as to be oriented in a direction intersecting the bottom portion of the recessed part.

According to the label of this invention, the tearing slit is formed along the direction intersecting the bottom portion of the recessed part (toward the direction intersecting the bottom portion of the recessed part). It is therefore possible to transmit a force applied to the detachable part from an upstream side of aforementioned tearing direction along the edge portion of the detachable part forming the recessed part and redirect the force from the bottom portion of the recessed part into the intersecting direction, so that the force is transmitted to the tearing slit. Thus, according to this construction, the force applied to the detachable part can be efficiently transmitted to the tearing slit as a force acting along the tearing direction, so that the base part and the detachable part can easily be torn apart.

One possible approach to efficiently transmitting the force applied to the detachable part might be to form the tearing slit on an extended line of the edge of the tearing slit constituting a side portion of the recessed part (or the portion located more outward than the bottom portion). This approach however has had a problem that the force applied to the detachable part would not be transmitted to the tearing slit but toward the bottom portion in a boundary area between the side portion and the bottom portion, thereby producing a problem that the base part and the detachable part would be torn apart from the bottom portion.

Conversely, another possible approach might be to form the tearing slit on an extended line of the edge portion of the base part constituting a side portion of the recessed part. In this case, however, there is a likelihood that the force applied to the detachable part acts as a force which tears apart the label at the bottom portion before the force reaches a boundary area between the side portion and the bottom portion.

According to the label of the present invention, the tearing slit is so formed as to intersect the bottom portion of the recessed part, so that the force applied to the detachable part can be efficiently transmitted to the tearing slit as a force acting along the tearing direction and, as a consequence, the base part and the detachable part can easily be torn apart.

Here, the expression concerning the tearing slit that "makes the edge portion of the base part and the detachable part tearable apart" refers not only to an arrangement in which the edge portion of the base part and the detachable part is already torn apart over a specified range but also to an arrangement in which a slit passing through the base part and the detachable part in a thickness direction thereof is formed at a downstream position of the tearing direction at an extremely small distance from the edge portion of the base part and the detachable part. In other words, the expression includes an arrangement in which the slit is formed to allow the base part and the detachable part to be torn apart by as much as the extremely small distance when a specific force is applied to the tab portion.

Also, the expression "the direction intersecting the bottom portion of the recessed part" refers to a direction other than a tangential direction of the bottom portion having a rounded shape, wherein the direction along the tearing slit intersects the bottom portion at a specific angle.

In the label, it is preferable that the perforation be laid out closer to the base part than the tearing slit, the tearing slit extend in the direction intersecting the bottom portion in the proximity of a bottommost point thereof so that an angle formed between the tearing slit and the bottom portion, opening toward the detachable part, becomes an obtuse angle, and the tearing slit be shaped to further extend, also forming an obtuse angle with the tearing direction along the perforation.

According to this construction, a tearing start point of the tearing slit and the perforation are vertically offset and the tearing slit forms obtuse angles with both the rounded bottom portion and the tearing direction along the perforation, so that a force applied to the detachable part along the tearing direction can be smoothly transmitted all the way along an edge of the detachable part forming the recessed part, the tearing slit and the perforation in this order. Therefore, according to the construction, it is possible to prevent such a problem that a portion other than the tear-off line breaks in an initial stage of lifting the detachable part.

Generally speaking, when the recessed part is formed in an edge portion of the detachable part and the tear-off line is formed along this recessed part, it is preferable, in principle, to form the recessed part to have a pointed bottom and to arrange the tear-off line to extend from this edge portion for neatly tearing off the detachable part from the base part.

In a process of manufacturing labels, however, each label is formed into a desired contour by punching a sheet by use of a cutting tool and it is difficult to configure the cutting tool to have an acutely pointed part in a portion corresponding to the bottom of the recessed part. Thus, from a viewpoint of cost-effectiveness, it is inevitable to form a slightly rounded shape in the bottom of the recessed part.

According to the principle, it is preferable to form the tear-off line extending from a bottommost point the rounded shape. In this case, however, the force applied to the detachable part will be redirected by approximately 90 degrees at the bottommost point. Therefore, if the tear-off line is formed to simply extend from the bottommost point of the rounded shape, there has been a possibility that a portion other than the tear-off line may break.

Under such circumstances, the present applicant has devised a layout in which the tearing start point is located in the proximity of the bottommost point of the rounded shape and the perforation is shifted slightly toward the base part than the rounded shape. With this arrangement, the force applied to the detachable part is transmitted from the arc-shaped segment of the bottom portion through the tearing slit, and from the tearing slit through the perforation, in two steps along gently changing directions.

Thus, according to the label of the present invention, the tearing slit formed along the direction interconnecting the bottom portion in the proximity of the bottommost point thereof (in the direction interconnecting the bottom portion in the proximity of the bottommost point thereof) forms obtuse angles with the bottom portion and the tearing direction along the perforation. It is therefore possible to neatly tear off the detachable part from the base part while preventing breakage of other portions of the label than the tear-off line.

In the label, it is preferable that there be formed a tab portion in the detachable part by not providing an adhesive layer on a rear surface of the detachable part at an upstream end of the tearing direction.

According to this construction, there be formed the tab portion at the upstream end of the tearing direction, so that the user can easily tear off the detachable part from the base part by holding the tab portion.

In the label, it is preferable that the tearing slit include an introductory portion which intersects the bottom portion at an obtuse angle and a bent portion which bends away from the introductory portion at an obtuse angle and is arranged on a line extended in the tearing direction along the perforation.

According to this construction, it is possible to transmit the force applied to the tab portion to the perforation in a reliable fashion by the introductory portion and the bent portion of the tearing slit.

Furthermore, the present invention discussed in the foregoing embodiments provides a storage container including a container body, a cap for sealing the container body which can be unsealed by operating the cap in a specified opening direction thereof, and the label, the storage container being characterized in that the base part of the label is attached to the container body and the detachable part of the label is attached to the cap under conditions where the tearing direction of the tear-off line of the label aligns with the opening direction of the cap.

According to this invention, the label is attached to the container body and the cap under conditions where the opening direction of the cap aligns with the tearing direction of the tear-off line, so that the detachable part and the base part can be torn apart by operating the cap in the opening direction thereof.

INDUSTRIAL APPLICABILITY

According to the present invention, it is possible to enable a user to recognize characteristic information necessary when using a medicine bag in a reliable fashion.

The invention claimed is:

1. A medicine bag comprising:

a container body accommodating medicines in an internal space thereof, the container body having a hanging hole formed in one end of a sealing portion defining the internal space, the hanging hole passing through the sealing portion from a front surface of the container body to a rear surface of the container body;

a port formed at the other end of the container body; and a label attached to only the front surface of the container body by an adhesive layer, the label including:

a base part indicating thereon basic information including at least information on ingredients of the medicines accommodated in the medicine bag, and the base part being attached to the container body; and a detachable part detachably joined to the base part, the detachable part indicating thereon characteristic information including at least directions on use of the medicine bag, wherein the detachable part of the label is detachably joined to the container body by an adhesive layer applied on a rear surface of the detachable part excepting a region corresponding to the hanging hole, and the medicines in the container body are discharged through the port under conditions where the container body is suspended by the hanging hole.

2. The medicine bag as recited in claim 1, wherein the base part and the detachable part are made tearable apart along a tear-off line having a defined tearing direction, and there is formed a tab portion in the detachable part by not providing an adhesive layer on a rear surface of the detachable part at an upstream end of the tearing direction.

3. The medicine bag as recited in claim 2, wherein there formed a recessed part having a rounded bottom portion in an edge portion of the base part and the detachable part, the bottom portion extending along both of the base part and the detachable part, and the tear-off line includes a tearing slit which makes the edge portion of the base part and the detachable part tearable from each other at the upstream end of the tearing direction and a perforation located downstream of the tearing slit along the tearing direction, wherein the tearing slit is so arranged as to be oriented in a direction intersecting the bottom portion of the recessed part.

4. The medicine bag as recited in claim 3, wherein the perforation is laid out closer to the base part than the tearing slit, the tearing slit extends in the direction intersecting the bottom portion in the proximity of a bottommost point thereof so that an angle formed between the tearing slit and the bottom portion, opening toward the detachable part, becomes an obtuse angle, and the tearing slit is shaped to further extend, also forming an obtuse angle with the tearing direction along the perforation.

5. The medicine bag as recited in claim 4, wherein the tearing slit includes an introductory portion which intersects the bottom portion at an obtuse angle and a bent portion which bends away from the introductory portion at an obtuse angle and is arranged on a line extended in the tearing direction along the perforation.

6. The medicine bag as recited in claim 5, wherein the detachable part includes a first detachable piece and a second detachable piece which are joined splittably from each other along a second tear-off line having a defined tearing direction intersecting the tearing direction between the base part and the detachable part, and the first detachable piece is configured to be attachable to such an area of the medicine bag that it becomes difficult to use the medicine bag when a surface of the area is covered.

7. The medicine bag as recited in claim 5, wherein the detachable part includes a first detachable piece and a second detachable piece which are already separated by a slit extending along a direction intersecting the tearing direction, the first detachable piece is configured to be attachable to such an area of the medicine bag that it becomes difficult to use the medicine bag when a surface of the area is covered, the recessed part and the tearing slit are formed in each of opposite edge portions of the base part and the detachable part, and opposite tearing directions are defined on the tear-off line in a range from one of these recessed parts to the slit and in a range from the other of these recessed parts to the slit.

8. The medicine bag as recited in claim 7, wherein the second detachable piece indicates the basic information.

9. The medicine bag as recited in claim 1, wherein the detachable part includes a first connected section detachably joined to the base part and a second connected section detachably joined to the first connected section, and the second connected section is configured to be attachable to such an area of the medicine bag that it becomes difficult to use the medicine bag when a surface of the area is covered.

10. The medicine bag as recited in claim 9, wherein the first connected section and the second connected section individually indicate the characteristic information.

11. The medicine bag as recited in claim 10, wherein the characteristic information includes at least one of such pieces of information that use of the medicines in the medicine bag for injection purposes must be prohibited and the medicine bag must be used after two kinds of medicines accommodated in the medicine bag have been mixed.

12. The medicine bag as recited in claim 1, wherein the base part of the label is attached to a front surface of the container body, a middle portion of the detachable part of the label is attached to the port, and an extreme end portion of the detachable part is attached to a rear surface of the container body.

13. The medicine bag as recited in claim 1, wherein the sealing portion is formed by joining a pair of sheets.

14. A medicine bag comprising:

a label including:

a base part indicating thereon basic information including at least information on ingredients of the medicines accommodated in the medicine bag; and a detachable part detachably joined to the base part, the detachable part being so shaped as to be attachable to such an area of the medicine bag that it becomes difficult to use the medicine bag when a surface of the area is covered, and indicating thereon characteristic information including at least directions on use of the medicine bag;

a container body accommodating medicines in an internal space thereof, the container body having a hanging hole formed in one end of a sealing portion defining the internal space, the hanging hole passing through the sealing portion from a front surface of the container body to a rear surface of the container body; and a port formed at the other end of the container body;

wherein the detachable part of the label is so attached as to cover at least part of the port, and the medicines in the container body are discharged through the port under conditions where the container body is suspended by the hanging hole, and wherein the label is attached to only the front surface of the container body by an adhesive layer, and the detachable part of the label is detachably joined to the container body by an adhesive layer applied on a rear surface of the detachable part excepting a region corresponding to the hanging hole.

15. A storage container comprising:

a container body having a hanging hole formed in one end of a sealing portion defining the internal space, the hanging hole passing through the sealing portion from a front surface of the container body to a rear surface of the container body;

a cap for sealing the container body which can be unsealed by operating the cap in a specified opening direction thereof; and a label including:

a base part; and a detachable part detachably joined to the base part along a tear-off line having a defined tearing direction;

a recessed part having a rounded bottom portion in an edge portion of the base part and the detachable part, the bottom portion extending along both of the base part and the detachable part, and the tear-off line including a tearing slit which makes the edge portion of the base part and the detachable part tearable from each other at an upstream end of the tearing direction and a perforation located downstream of the tearing slit along the tearing direction, the tearing slit being so arranged as to be oriented in a direction intersecting the bottom portion of the recessed part;

wherein the base part of the label is attached to the container body and the detachable part of the label is attached to the cap under conditions where the tearing direction of the tear-off line of the label aligns with the opening direction of the cap, and wherein the label is attached to only the front surface of the container body by an adhesive layer, and the detachable part of the label is detachably joined to the container body by an adhesive layer applied on a rear surface of the detachable part excepting a region corresponding to the hanging hole.

* * * * *